(12) United States Patent
Borzilleri et al.

(10) Patent No.: US 7,084,160 B2
(45) Date of Patent: Aug. 1, 2006

(54) HETEROCYCLIC INHIBITORS OF KINASES

(75) Inventors: Robert M. Borzilleri, New Hope, PA (US); Rajeev S. Bhide, Princeton Jct, NJ (US); John S. Tokarski, Princeton, NJ (US); Peter Zheng, Lawrenceville, NJ (US); Ligang Qian, Hopewell, NJ (US); Zhen-Wei Cai, Belle Meade, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 388 days.

(21) Appl. No.: 10/464,139

(22) Filed: Jun. 18, 2003

(65) Prior Publication Data

US 2004/0077696 A1    Apr. 22, 2004

Related U.S. Application Data

(60) Provisional application No. 60/390,813, filed on Jun. 20, 2002.

(51) Int. Cl.
*A61K 31/44* (2006.01)
*C07D 417/12* (2006.01)

(52) U.S. Cl. ............... 514/342; 546/268.1; 546/269.7; 546/270.7

(58) Field of Classification Search ............ 546/268.1, 546/269.7, 270.7; 514/342
See application file for complete search history.

(56) References Cited

U.S. PATENT DOCUMENTS

| | | | | |
|---|---|---|---|---|
| 6,040,321 | A * | 3/2000 | Kim et al. | 514/369 |
| 6,214,852 | B1 * | 4/2001 | Kim et al. | 514/369 |
| 6,262,096 | B1 | 7/2001 | Kim et al. | |
| 2003/0069244 | A1 | 4/2003 | Leftheris et al. | |

OTHER PUBLICATIONS

Kim et al (2001): STN International CAPLUS database, Columbus (Ohio), Accession No.: 2001:521913.*
Fan et al., Trend Pharcol. Sci., vol. 16, pp. 57-66 (1995).
Folkman, Nature Medicine, vol. 1, pp. 27-31 (1995).
Cullinan-Bove et al., Endocrinology, vol. 133, pp. 829-837 (1993).
Senger et al., Cancer and Metastasis Reviews, vol. 12, pp. 303-324 (1993).
DeVries et al., Science, vol. 255, pp. 989-991 (1992).
Terman et al., Biochem. Biophys. Res. Comm., vol. 187, pp. 1579-1586 (1992).
Jakeman et al., Endocrinology, vol. 133, pp. 848-859 (1993).
Koich et al., Breast Cancer Research and Treatment, vol. 36, pp. 139-155 (1995).
Connolly et al., J. Biol. Chem., vol. 264, pp. 20017-20024 (1989).

* cited by examiner

*Primary Examiner*—Golam M. M. Shameem
(74) *Attorney, Agent, or Firm*—Elliott Korsen

(57) ABSTRACT

The present invention provides compounds of formula I

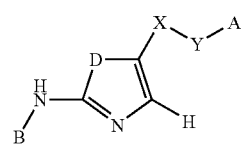

and pharmaceutically acceptable salts thereof.

The formula I compounds inhibit the tyrosine kinase activity of growth factor receptors such as VEGFR-2, FGFR-1, thereby making them useful as anti-cancer agents. The formula I compounds are also useful for the treatment of other diseases associated with signal transduction pathways operating through growth factor receptors.

4 Claims, No Drawings

HETEROCYCLIC INHIBITORS OF KINASES

This application claims priority to U.S. Provisional Application Ser. No. 60/390,813 filed Jun. 20, 2002, the entirety of which is incorporated herein by reference.

FIELD OF THE INVENTION

This invention relates to compounds that inhibit the tyrosine kinase activity of growth factor receptors such as VEGFR-2, FGFR-1 and PDGFR-β.

BACKGROUND OF THE INVENTION

Normal angiogenesis plays an important role in a variety of processes including embryonic development, wound healing, obesity and several components of female reproductive function. Undesirable or pathological angiogenesis had been associated with disease states including diabetic retinopathy, psoriasis, cancer, rheumatoid arthritis, atheroma, Kaposi's sarcoma and haemangioma (Fan et al, 1995, Trend Pharmacol. Sci. 16: 57–66; Folkman, 1995, Nature Medicine 1: 27–31). Alteration of vascular permeability is thought to play a role in both normal and pathophysiological processes (Cullinan-Bove et al, 1993, Endocrinology 133: 829–837; Senger et al, 1993 Cancer and Metastasis Reviews, 12: 303–324).

Receptor tyrosine kinases (RTKs) are important in the transmission of biochemical signals across the plasma membrane of cells. These transmembrane molecules characteristically consist of an extracellular ligand-binding domain connected through a segment in the plasma membrane to an intracellular tyrosine kinase domain. Binding of ligand to the receptor results in stimulation of the receptor-associated tyrosine kinase activity that leads to phosphorylation of tyrosine residues on both the receptor and other intracellular proteins, leading to a variety of cellular responses. To date, at least nineteen distinct RTK subfamilies, defined by amino acid sequence homology, have been identified. One of these subfamilies is presently comprised by the fms-like tyrosine kinase receptor, Flt or Flt1 (VEGFR-1), the kinase insert domain-containing receptor, KDR (also referred to as Flk-1 or VEGFR-2), and another fms-like tyrosine kinase receptor, Flt4 (VEGFR-3). Two of these related RTKs, Flt and KDR, have been shown to bind vascular endothelial growth factor (VEGF) with high affinity (De Vries et al, 1992, Science 255: 989–991; Terman et al, 1992, Biochem. Biophys. Res. Comm. 1992, 187: 1579–1586). Binding of VEGF to these receptors expressed in heterologous cells had been associated with changes in the tyrosine phosphorylation status of cellular proteins and calcium fluxes. VEGF, along with acidic and basic fibroblast growth factor (aFGF & bFGF) have been identified as having in vitro endothelial cell growth promoting activity. By virtue of the restricted expression of its receptors, the growth factor activity of VEGF, in contrast to that of the FGFs, is relatively specific towards endothelial cells. Recent evidence indicates that VEGF is an important stimulator of both normal and pathological angiogenesis (Jakeman et al, 1993, Endocrinology, 133: 848–859; Kolch et al, 1995, Breast Cancer Research and Treatment, 36: 139–155) and vascular permeability (Connolly et al, 1989, J. Biol. Chem. 264: 20017–20024).

In adults, endothelial cells have a low proliferation index except in cases of tissue remodeling, such as wound healing and the female reproductive cycle, and adipogenesis. However in pathological states such as cancer, inherited vascular diseases, endometriosis, psoriasis, arthritis, retinopathies and atherosclerosis, endothelial cells are actively proliferating and organizing into vessels. Upon exposure to angiogenic stimuli with growth factors such as VEGF and bFGF, endothelial cells re-enter the cell cycle, proliferate, migrate and organize into a three-dimensional network. The ability of tumors to expand and metastasize is dependent upon the formation of this vascular network.

Binding of VEGF or bFGF to their corresponding receptor results in dimerization, autophosphorylation on tyrosine residues and enzymatic activation. These phosphotyrosine residues serve as "docking" sites for specific downstream signaling molecules and enzymatic activation results in proliferation of endothelial cells. Disruption of these pathways should inhibit endothelial cell proliferation. Disruption of the FGFR-1 pathway should also affect tumor cell proliferation since this kinase is activated in many tumor types in addition to proliferating endothelial cells. Finally, recent evidence also suggests that disruption of VEGF signaling inhibits endothelial cell migration, a critical process in vascular network formation.

The over-expression and activation of VEGFR-2, FGFR-1 and PDGFR-β in tumor-associated vasculature has suggested a role for these molecules in tumor angiogenesis. Angiogenesis and subsequent tumor growth is inhibited by antibodies directed against VEGF ligand and VEGF receptors, and by truncated (lacking a transmembrane sequence and cytoplasmic kinase domain) soluble VEGFR-2 receptors. Dominant mutations introduced into either VEGFR-2 or FGFR-1 which result in a loss of enzymatic activity inhibits tumor growth in vivo. Antisense targeting of these receptors or their cognate ligands also inhibits angiogenesis and tumor growth. Recent evidence has elucidated, in part, the temporal requirements of these receptors in tumor growth. It appears that VEGF signaling is critical in early tumor growth and bFGF is more important at a later time associated with tumor expansion.

SUMMARY OF THE INVENTION

A compound of formula I

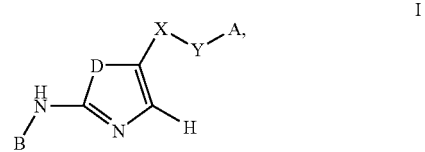

its enantiomers, diastereomers, and pharmaceutically acceptable salts, prodrugs and solvates thereof, wherein, A and B are independently selected from the group consisting of aryl, substituted aryl, heteroaryl, substituted heteroaryl, heterocyclo, substituted heterocyclo, lower alkyl, arylalkyl, alkylaryl and alkylheteroaryl;

X and Y are independently selected from the group consisting of $R^1CR^2$, S, O, $SO_2$, SO and $NR^3$, with the proviso that at least one of X and Y is $R^1CR^2$;

D is selected from the group consisting of S, O, and $NR^4$;

$R^1$, $R^2$, $R^3$ and $R^4$ are independently selected from the group consisting of hydrogen, alkyl, substituted alkyl, aryl, substituted aryl, heterocyclo, substituted heterocyclo, aralkyl, arylalkyl, substituted aralkyl, $COR^5$ and $SO_2R^6$; and, $R^5$ and $R^6$ are independently selected from the group consisting of alkyl, substituted alkyl, aryl, substituted aryl, heterocyclo, substituted heterocyclo, heteroaryl, substituted heteroaryl, aralkyl, substituted aralkyl, heterocycloalkyl and substituted heterocycloalkyl.

The invention also comprises a pharmaceutical composition having a compound of formula I as the active ingredient in addition to a pharmaceutically acceptable carrier.

The invention further provides a method of inhibiting protein kinase activity of growth factor receptors which comprises administering to a mammalian species in need thereof, an effective protein kinase inhibiting amount of a compound of formula I.

DESCRIPTION OF THE INVENTION

In accordance with the present invention, compounds of formula I

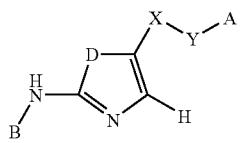

their enantiomers, diastereomers, and pharmaceutically acceptable salts, prodrugs and solvates thereof inhibit the tyrosine kinase activity of growth factor receptors such as VEGFR-2, FGFR-1 and PDGFR-β.

In formula I and throughout the specification, the substituents are defined as follows:

A and B are independently selected from the group consisting of aryl, substituted aryl, heteroaryl, substituted heteroaryl, heterocyclo, substituted heterocyclo, lower alkyl, arylalkyl, alkylaryl and alkylheteroaryl.

X and Y are independently selected from the group consisting of $R^1CR^2$, S, O, $SO_2$, SO and $NR^3$, with the proviso that at least one of X and Y is $R^1CR^2$.

D is selected from the group consisting of S, O, and $NR^4$.

$R^1$, $R^2$, $R^3$ and $R^4$ are independently selected from the group consisting of hydrogen, alkyl, substituted alkyl, aryl, substituted aryl, heterocyclo, substituted heterocyclo, aralkyl, arylalkyl, substituted aralkyl, $COR^5$ and $SO_2R^6$.

$R^5$ and $R^6$ are independently selected from the group consisting of alkyl, substituted alkyl, aryl, substituted aryl, heterocyclo, substituted heterocyclo, heteroaryl, substituted heteroaryl, aralkyl, substituted aralkyl, heterocycloalkyl and substituted heterocycloalkyl.

In a preferred embodiment compounds of the invention are compounds of formula I wherein X is $R^1CR^2$; Y is selected from the group consisting of $R^1CR^2$; $NR^3$ and S; and, A is selected from the group consisting of substituted aryl, aryl, substituted heterocyclo, heterocyclo, substituted heteroaryl and heteroaryl.

In another preferred embodiment, the invention comprises compounds of formula I wherein X is $R^1CR^2$; Y is selected from the group consisting of $R^1CR^2$; $NR^3$ and S; $R^1$ and $R^2$ are hydrogen; $R^3$ is selected from the group consisting of hydrogen and $SO_2R^6$; $R^6$ is a lower alkyl; and, A is selected from the group consisting of substituted aryl, aryl, substituted heterocyclo, heterocyclo, substituted heteroaryl and heteroaryl.

In another preferred embodiment, the invention comprises compounds of formula I wherein X is $R^1CR^2$; Y is $R^1CR^2$ or $NR^3$; $R^3$ is hydrogen; D is sulfur, and A is selected from the group consisting of substituted aryl, substituted heterocyclo and substituted heteroaryl.

In yet another preferred embodiment, the invention comprises compounds of formula I wherein X is $R^1CR^2$; Y is $R^1CR^2$ or $NR^3$; $R^1$, $R^2$ and $R^3$ are hydrogen; D is sulfur; A is an amide substituted aryl; and, B is heteroaryl. A preferred amide group is (C=O)$NR^7$ wherein $R^7$ is selected from cycloalkyl, substituted alkyl, aryl, substituted aryl, heterocyclo, substituted heterocyclo, heteroaryl and substituted heteroaryl.

In still yet another preferred embodiment, the invention comprises compounds of formula I wherein A is a substituted aryl and said aryl is substituted with at least one of the group consisting of cyclopropyl amide, halo, cyano, and lower alkyl. A preferred aryl is phenyl.

Preferred compounds of the invention are compounds of the formula

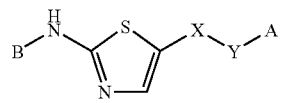

B is a pyridinyl group optionally substituted with 1-4 substituents as disclosed herein;

A is substituted aryl.

X and Y are independently selected from the group consisting of $R^1CR^2$, S, O, $SO_2$, SO and $NR^3$, with the proviso that at least one of X and Y is $R^1CR^2$; its enantiomers, diastereomers, and pharmaceutically acceptable salts, prodrugs and solvates thereof, In a preferred embodiment, the invention comprises a compound of formula II wherein R is a substituted or unsubstituted benzamide.

Preferred compounds of the invention include 2,4-Difluoro-N-methyl-5-{[2-(Pyridin-2-ylamino)-thiazole-5-ylmethyl]-amino}-benzamide;

4-Fluoro-N-methyl-3-{[2-(pyridin-2-ylamino)-thiazol-5-ylmethyl]-amino}-benzamide;

N-Cyclopropyl-4-fluoro-3-{[2-(pyridin-2-ylamino)-thiazol-5-ylmethyl]-amino}-benzamide;

N-Cyclopropyl-4-fluoro-3-{2-[2-(pyridin-2-ylamino)-thiazol-5-yl]-ethyl}-benzamide;

N-Cyclopropyl-2,4-difluoro-5-{[2-(4-methyl-pyridin-2-ylamino)-thiazol-5-ylmethyl]-amino}-benzamide;

N-Cyclopropyl-2,4-difluoro-5-{[2-(pyridin-2-ylamino)-thiazol-5-ylmethyl]-amino}-benzamide N-Cyclopropyl-2,4-difluoro-5-({2-[5-(4-methyl-piperazine-1-carbonyl)-pyridin-2-ylamino]-thiazol-5-ylmethyl}-amino)-benzamide;

6-{5-[(5-Cyclopropylcarbamoyl-2,4-difluoro-phenylamino)-methyl]-thiazol-2-ylamino}-N-(2-dimethylamino-ethyl)-N-methylnicotinamide;

6-{5-[2-(5-Cyclopropylcarbamoyl-2-fluoro-phenyl)-ethyl]-thiazol-2-ylamino}-N-(2-ethylamino-ethyl)-nicotinamide;

4-Fluoro-3-{[2-(pyridin-2-ylamino)-thiazol-5-ylmethyl]-amino}-N-thiophen-2-ylmethylbenzamide;

N-Benzyl-4-fluoro-3-{[2-(pyridin-2-ylamino)-thiazol-5-ylmethyl]-amino}-benzamide;

4-Fluoro-3-{[2-(pyridin-2-ylamino)-thiazol-5-ylmethyl]-amino}-N-pyridin-2-ylmethylbenzamide;

4-Fluoro-N-(3-morpholin-4-yl-propyl)-3-{[2-(pyridin-2-ylamino)-thiazol-5-ylmethyl]-amino}-benzamide;

4-Fluoro-N-prop-2-ynyl-3-{[2-(pyridin-2-ylamino)-thiazol-5-ylmethyl]-amino}-benzamide;

4-Fluoro-N-isoxazol-3-yl-3-{[2-(pyridin-2-ylamino)-thiazol-5-ylmethyl]-amino}-benzamide 4-Fluoro-N-(5-methyl-isoxazol-3-yl)-3-{[2-(pyridin-2-ylamino)-thiazol-5-ylmethyl]-amino}-benzamide; and N-(2,2-Difluoro-3-morpholin-4-yl-propyl)-4-fluoro-3-{[2-(pyridin-2-ylamino)-thiazol-5-ylmethyl]-amino}-benzamide The invention also provides a pharmaceutical composition comprising a compound of formula I or II and a pharmaceutically acceptable carrier.

The invention also provides a pharmaceutical composition comprising a compound of formula I or II in combination with pharmaceutically acceptable carrier and an anti-cancer or cytotoxic agent. In a preferred embodiment said anti-cancer or cytotoxic agent is selected from the group consisting of linomide; inhibitors of integrin αvβ3 function; angiostatin; razoxane; tamoxifen; toremifene; raloxifene; droloxifene; iodoxifene; megestrol acetate; anastrozole; letrozole; borazole; exemestane; flutamide; nilutamide; bicalutamide; cyproterone acetate; gosereline acetate; leuprolide; finasteride; metalloproteinase inhibitors; inhibitors of urokinase plasminogen activator receptor function; growth factor antibodies; growth factor receptor antibodies such as Avastin® (bevacizumab) and Erbitux® (cetuximab); tyrosine kinase inhibitors; serine/threonine kinase inhibitors; methotrexate; 5-fluorouracil; purine; adenosine analogues; cytosine arabinoside; doxorubicin; daunomycin; epirubicin; idarubicin; mitomycin-C; dactinomycin; mithramycin; cis-platin; carboplatin; nitrogen mustard; melphalan; chlorambucil; busulphan; cyclophosphamide; ifosfamide nitrosoureas; thiotepa; vincristine; Taxol® (pacliatxel); Taxotere® (docetaxel); epothilone analogs; discodermolide analogs; eleutherobin analogs; etoposide; teniposide; amsacrine; topotecan; flavopyridols; biological response modifiers and proteasome inhibitors such as Velcade® (bortezomib).

The invention also provides a method of inhibiting protein kinase activity of growth factor receptors which comprises administering to a mammalian species in need thereof, a therapeutically effective protein kinase inhibiting amount of a compound of formula I or II.

Additionally, there is disclosed a method of inhibiting tyrosine kinase activity of at least one growth factor receptor such as which comprises administering to a mammalian species in need thereof, a therapeutically effective amount of a compound of formula I or II. In a preferred embodiment said growth factor receptor is selected from the group consisting of VEGFR-2, FGFR-1 and PDGFR-β.

Finally, there is disclosed a method for treating a proliferative disease, comprising administering to a mammalian species in need thereof, a therapeutically effective amount of a compound of formula I or II. In a preferred embodiment the proliferative disease is cancer.

The following are definitions of terms used in the present specification. The initial definition provided for a group or term herein applies to that group or term throughout the present specification individually or as part of another group, unless otherwise indicated.

The term "alkyl" refers to straight or branched chain unsubstituted hydrocarbon groups of 1 to 20 carbon atoms, preferably 1 to 7 carbon atoms. The expression "lower alkyl" refers to unsubstituted alkyl groups of 1 to 4 carbon atoms.

The term "substituted alkyl" refers to an alkyl group substituted by, for example, one to four substituents, such as, halo, hydroxy, alkoxy, oxo, alkanoyl, aryloxy, alkanoyloxy, amino, alkylamino, arylamino, aralkylamino, disubstituted amines in which the two amino substituents are selected from alkyl, aryl or aralkyl; alkanoylamino, aroylamino, aralkanoylamino, substituted alkanoylamino, substituted arylamino, substituted aralkanoylamino, thiol, alkylthio, arylthio, aralkylthio, alkylthiono, arylthiono, aralkylthiono, alkylsulfonyl, arylsulfonyl, aralkylsulfonyl, sulfonamido, e.g. $SO_2NH_2$, substituted sulfonamido, nitro, cyano, carboxy, carbamyl, e.g. $CONH_2$, substituted carbamyl e.g. CONHalkyl, CONHaryl, CONHaralkyl or cases where there are two substituents on the nitrogen selected from alkyl, aryl or aralkyl; alkoxycarbonyl, aryl, substituted aryl, guanidino and heterocyclos, such as, indolyl, imidazolyl, furyl, thienyl, thiazolyl, pyrrolidyl, pyridyl, pyrimidyl and the like. Where noted above where the substituent is further substituted it will be with alkyl, alkoxy, aryl or aralkyl.

The term "halogen" or "halo" refers to fluorine, chlorine, bromine and iodine.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The term "aralkyl" refers to an aryl group bonded directly through an alkyl group, such as benzyl.

The term "substituted aryl" refers to an aryl group substituted by, for example, one to four substituents such as alkyl, substituted alkyl, halo, trifluoromethoxy, trifluoromethyl, hydroxy, alkoxy, alkanoyl, alkanoyloxy, amino, alkylamino, aralkylamino, dialkylamino, alkanoylamino, thiol, alkylthio, ureido, nitro, cyano, carboxy, carboxyalkyl, carbamyl, amido, alkoxycarbonyl, alkylthiono, arylthiono, arylsulfonylamine, sulfonic acid, alkylsulfonyl, sulfonamido, aryloxy and the like. The substituent may be further substituted by hydroxy, alkyl, alkoxy, aryl, substituted aryl, substituted alkyl or aralkyl.

The term "heteroaryl" refers to an optionally substituted, aromatic group for example, which is a 4 to 7 membered monocyclic, 7 to 11 membered bicyclic, or 10 to 15 membered tricyclic ring system, which has at least one heteroatom and at least one carbon atom-containing ring, for example, pyridine, tetrazole, indazole.

The term "alkenyl" refers to straight or branched chain hydrocarbon groups of 2 to 20 carbon atoms, preferably 2 to 15 carbon atoms, and most preferably 2 to 8 carbon atoms, having one to four double bonds.

The term "substituted alkenyl" refers to an alkenyl group substituted by, for example, one to two substituents, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino, indolyl, imidazolyl, furyl, thienyl, thiazolyl, pyrrolidyl, pyridyl, pyrimidyl and the like.

The term "alkynyl" refers to straight or branched chain hydrocarbon groups of 2 to 20 carbon atoms, preferably 2 to 15 carbon atoms, and most preferably 2 to 8 carbon atoms, having one to four triple bonds.

The term "substituted alkynyl" refers to an alkynyl group substituted by, for example, a substituent, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino and heterocyclo, e.g. imidazolyl, furyl, thienyl, thiazolyl, pyrrolidyl, pyridyl, pyrimidyl and the like.

The term "cycloalkyl" refers to an optionally substituted, saturated cyclic hydrocarbon ring systems, preferably containing 1 to 3 rings and 3 to 7 carbons per ring which may be further fused with an unsaturated $C_3$–$C_7$ carbocylic ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more groups described above as alkyl substituents.

The terms "heterocycle", "heterocyclic" and "heterocyclo" refer to an optionally substituted, fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, dioxanyl, isothiazolidinyl, thictanyl, thiiranyl, triazinyl, and triazolyl, and the like.

Exemplary bicyclic hetrocyclic groups include 2,3-dihydro-2-oxo-1H-indolyl, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, indolyl, naphthyridinyl, phthalazinyl, piperonyl, purinyl, pyridopyridyl, quinazolinyl, tetrahydroquinolinyl, thienofuryl, thienopyridyl, thienothienyl, and the like.

Exemplary substituents include one or more alkyl or aralkyl groups as described above or one or more groups described above as alkyl substituents. Also included are smaller heterocyclos, such as, epoxides and aziridines.

The term "heteroatoms" shall include oxygen, sulfur and nitrogen.

The compounds of formula I may form salts which are also within the scope of this invention. Pharmaceutically acceptable (i.e. non-toxic, physiologically acceptable) salts are preferred, although other salts are also useful, e.g., in isolating or purifying the compounds of this invention.

The compounds of formula I may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be formed as known to those skilled in the art.

The compounds of formula I may form salts with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid and various others (e.g., nitrates, phosphates, borates, tartrates, citrates, succinates, benzoates, ascorbates, salicylates and the like). Such salts can be formed as known to those skilled in the art. In addition, zwitterions ("inner salts") may be formed.

All stereoisomers of the compounds of the instant invention are contemplated, either in admixture or in pure or substantially pure form. The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

Compounds of the formula I may also have prodrug forms. Any compound that will be converted in vivo to provide the bioactive agent (i.e., the compound for formulas I) is a prodrug within the scope and spirit of the invention.

Various forms of prodrugs are well known in the art. For examples of such prodrug derivatives, see:

a) *Design of Prodrugs,* edited by H. Bundgaard, (Elsevier, 1985) and *Methods in Enzymology,* Vol. 42, p. 309–396, edited by K. Widder, et al. (Acamedic Press, 1985);

b) *A Textbook of Drug Design and Development,* edited by Krosgaard-Larsen and H. Bundgaard, Chapter 5, "Design and Application of Prodrugs," by H. Bundgaard, p. 113–191 (1991);

c) H. Bundgaard, *Advanced Drug Delivery Reviews,* 8, 1–38 (1992);

It should further be understood that solvates (e.g., hydrates) of the compounds of formula I are also within the scope of the present invention. Methods of solvation are generally known in the art.

USE AND UTILITY

The present invention is based on the discovery that certain heterocycles are inhibitors of protein kinases. More specifically, they inhibit the effects of VEGF, a property of value in the treatment of disease states associated with angiogenesis and/or increased vascular permeability such as cancer. The invention relates to a pharmaceutical composition of compound of formula I, or pharmaceutically acceptable salt or hydrate thereof, and a pharmaceutically acceptable carrier in the treatment of hyperproliferative disorder in mammal. In particular, the said pharmaceutical composition is expected to inhibit the growth of those primary and recurrent solid tumors which are associated with VEGF, especially those tumors which are significantly dependent on VEGF for their growth and spread, including for example, cancers of the bladder, squamous cell, head, colorectal, oesophageal, gynecological (such as ovarian), pancreas, breast, prostate, lung, vulva, skin, brain, genitourinary tract, lymphatic system (such as thyroid), stomach, larynx and lung. In another embodiment, the compounds of the present invention are also useful in the treatment of noncancerous disorders such as diabetes, diabetic retinopathy, psoriasis, rheumatoid arthritis, obesity, Kaposi's sarcoma, haemangioma, acute and chronic nephropathies (including proliferative glomerulonephritis and diabetes-induced renal disease), atheroma, arterial restenosis, autoimmune diseases, acute inflammation and ocular diseases with retinal vessel proliferation, diabetic retinopathy, retinopathy of prematurity and macular degeneration. The invention also relates to prevention of blastocyte implantation in a mammal, treatment of atherosclerosis, excema, sclerodema, hemangioma. Compounds of the present invention posses good activity against VEGF receptor tyrosine kinase while possessing some activity against other tyrosine kinases.

Thus according to a further aspect of the invention there is provided the use of a compound of formula I, or a pharmaceutically acceptable salt thereof in the manufacture of a medicament for use in the production of an antiangiogenic and/or vascular permeability reducing effect in a warm-blooded animal such as a human being.

According to a further feature of the invention there is provided a method for producing an antiangiogenic and/or vascular permeability reducing effect in a mammalian species in need thereof, which comprises administering a therapeutically effective amount of a compound of formula I or a pharmaceutically acceptable salt thereof as defined herein before.

The antiproliferative, antiangiogenic and/or vascular permeability reducing treatment defined herein before may be applied as a sole therapy or may involve, in addition to a compound of the invention, one or more other substances and/or treatments. Such conjoint treatment may be achieved by way of the simultaneous, sequential or separate administration of the individual components of the treatment. The compounds of this invention may also be useful in combination with known anti-cancer and cytotoxic agents and treatments, including radiation. If formulated as a fixed dose, such combination products employ the compounds of this invention within the dosage range described below and the other pharmaceutically active agent within its approved dosage range. Compounds of formula I may be used sequentially with known anticancer or cytotoxic agents and treatment, including radiation when a combination formulation is inappropriate.

In the field of medical oncology it is normal practice to use a combination of different forms of treatment to treat each patient with cancer. In medical oncology the other component(s) of such conjoint treatment in addition to the antiproliferative, antiangiogenic and/or vascular permeability reducing treatment defined herein before may be: surgery, radiotherapy or chemotherapy. Such chemotherapy may cover three main categories of therapeutic agent:

(i) antiangiogenic agents that work by different mechanisms from those defined hereinbefore (for example, linomide, inhibitors of integrin $\alpha v\beta 3$ function, angiostatin, razoxane);

(ii) cytostatic agents such as antiestrogens (for example tamoxifen, toremifene, raloxifene, droloxifene, iodoxifene), progestogens (for example megestrol acetate), aromatase inhibitors (for example anastrozole, letrozole, borazole, exemestane), antihormones, antiprogestogens, antiandrogens (for example flutamide, nilutamide, bicalutamide, cyproterone acetate), LHRH agonists and antagonists (for example goserelin acetate, leuprolide), inhibitors of testosterone $5\alpha$-dihydroreductase (for example finasteride), farnesyltransferase inhibitors, anti-invasion agents (for example metalloproteinase inhibitors like marimastat and inhibitors of urokinase plasminogen activator receptor function) and inhibitors of growth factor function, (such growth factors include for example EGF, FGF, platelet derived growth factor and hepatocyte growth factor such inhibitors include growth factor antibodies, growth factor receptor antibodies such as Avastin® (bevacizumab) and Erbitux® (cetuximab); tyrosine kinase inhibitors and serine/threonine kinase inhibitors); and (iii) antiproliferative/antineoplastic drugs and combinations thereof, as used in medical oncology, such as antimetabolites (for example antifolates like methotrexate, fluoropyrimidines like 5-fluorouracil, purine and adenosine analogues, cytosine arabinoside); Intercalating antitumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide nitrosoureas, thiotepa; antimitotic agents (for example vinca alkaloids like vincristine and taxoids like Taxol® (paclitaxel), Taxotere® (docetaxel) and newer microbtubule agents such as epothilone analogs, discodermolide analogs, and eleutherobin analogs); topoisomerase inhibitors (for example epipodophyllotoxins like etoposide and teniposide, amsacrine, topotecan); cell cycle inhibitors (for example flavopyridols); biological response modifiers and proteasome inhibitors such as Velcade® (bortezomib).

As stated above, the formula I compounds of the present invention are of interest for their antiangiogenic and/or vascular permeability reducing effects. Such compounds of the invention are expected to be useful in a wide range of disease states including cancer, diabetes, psoriasis, rheumatoid arthritis, Kaposi's sarcoma, haemangioma, obesity, acute and chronic nephropathies, atheroma, arterial restenosis, autoimmune diseases, acute inflammation and ocular diseases associated with retinal vessel proliferation such as diabetic retinopathy.

More specifically, the compounds of formula I are useful in the treatment of a variety of cancers, including (but not limited to) the following:

carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma;

hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burkett's lymphoma;

hematopoietic tumors of myeloid lineage, including acute and chronic myelogenous leukemias, myelodysplastic syndrome and promyelocytic leukemia;

tumors of mesenchymal origin, including fibrosarcoma and rhabdomyosarcoma;

tumors of the central and peripheral nervous system, including astrocytoma, neuroblastoma, glioma and schwannomas; and other tumors, including melanoma, seminoma, teratocarcinoma, osteosarcoma, xenoderoma pigmentosum, keratoctanthoma, thyroid follicular cancer and Kaposi's sarcoma.

Due to the key role of kinases in the regulation of cellular proliferation in general, inhibitors could act as reversible cytostatic agents which may be useful in the treatment of any disease process which features abnormal cellular proliferation, e.g., benign prostate hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, and fungal infections.

Compounds of formula I may induce or inhibit apoptosis. The apoptotic response is aberrant in a variety of human diseases. Compounds of formula I, as modulators of apoptosis, will be useful in the treatment of cancer (including but not limited to those types mentioned hereinabove), viral infections (including but not limited to herpevirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

The compounds of formula I are especially useful in treatment of tumors having a high incidence of tyrosine kinase activity, such as colon, lung, and pancreatic tumors. By the administration of a composition (or a combination) of the compounds of this invention, development of tumors in a mammalian host is reduced.

Compounds of formula I may also be useful in the treatment of diseases other than cancer that may be associated with signal transduction pathways operating through growth factor receptors such as VEGFR-2.

The compounds of this invention may be formulated with a pharmaceutical vehicle or diluent for oral, intravenous or subcutaneous administration. The pharmaceutical composition can be formulated in a classical manner using solid or liquid vehicles, diluents and additives appropriate to the desired mode of administration. Orally, the compounds can be administered in the form of tablets, capsules, granules, powders and the like. The compounds may be administered in a dosage range of about 0.05 to 200 mg/kg/day, preferably less than 100 mg/kg/day, in a single dose or in 2 to 4 divided doses.

BIOLOGICAL ASSAYS

The following assays can be employed in ascertaining the activity of a compound as an inhibitor of the tyrosine kinase activity of growth factor receptors.

| VEGFR-2 and FGFR-1 Kinase assays: | | |
|---|---|---|
| Reagents | Final Concentration | |
| Stock Solution | VEGFR-2 | FGFR-1 |
| Tris pH 7.0 | 20 mM | 20 mM |
| BSA 10 mg/ml | 25 µg/ml | 25 µg/ml |
| MnCl$_2$ (1 M) | 1.5 mM | 0.5 mM |
| MgCl$_2$ (1 M) | — | 0.5 mM |
| DTT (1 M) | 0.5 mM | 0.5 mM |
| Enzyme Stock in 10% glycerol (1 mg/ml) | 7.5 ng/rxn | 30 ng/rxn |
| Poly glu/tyr (10 mg/ml) | 75 µg/ml | 30 µg/ml |
| ATP (1 mM) | 2.5 µM | 1.0 µM |
| γ-ATP (10 µCi/µl) | 0.5 µCi/ml | 0.5 µCi/ml |

Incubation mixtures employed for VEGFR-2 or FGFR-1 assay contain the synthetic substrate poly glu/tyr, (4:1), ATP, ATP-γ-$^{33}$P and buffer containing Mn$^{++}$ and/or Mg$^{++}$, DTT, BSA, and Tris buffer. The reaction is initiated by addition of enzyme and after 60 minutes at RT is terminated by the addition of 30% TCA to a final concentration of 15% TCA. Inhibitors are brought to 10 mM in 100% DMSO. Assays are prepared in a 96 well format in quadruplicate. Compounds are diluted 1:500 in 100% DMSO and then 1:10 in water for a final DMSO concentration of 10%. 10 µL are added to rows B-H in a 96 well format of 10% DMSO. 20 µl of compound is added to row A at a concentration 5 fold higher than running conditions. Ten µL are transferred to each row followed by six serial dilutions with mixing, and at row F 10 µL are discarded. Row G is a control with no compound and row H is no compound and no enzyme control. Enzyme and substrate are delivered using a Tomtec Quadra station.

Plates are covered with sticky plate tops, incubated at 27° C. for 60 minutes, and then acid precipitated with TCA for 20 minutes on ice. The precipitate is transferred to UniFilter-96, GF/C microplates using either a Tomtec or Packard FilterMate harvester. Activity is determined by quantitating the incorporated radioactivity using a Packard TopCount Microplate Scintillation Counter following the addition of Microscint-20 cocktail into each dried well of the UniFilter microplates.

PDGFR-β Assay

The PDGFR-β human receptor tyrosine kinase was assayed using the synthetic polymer poly(Glu$_4$/Tyr) (Sigma Chemicals) as a phosphoacceptor substrate. Each reaction mixture consisted of a total volume of 50 µl and contained 200 ng of baculovirus expressed enzyme, 64 µg/ml poly (Glu$_4$/Tyr), 3.6 µM of ATP, and 0.7 µCi of [γ-$^{33}$P]ATP. The mixture also contained 20 nM HEPES pH 7.0 buffer, 5 mM MnCl$_2$, 150 mM NaCl, 0.5 mM DDT, and 25 µg/ml bovine serum albumin. The reaction mixtures were incubated at 27° C. for 60 minutes and kinase activity was determined by quantitation of the amount of radioactive phosphate transferred to the poly(Glu$_4$/Tyr) substrate. Incorporation was measured by the addition of cold trichloroacetic acid. Precipitates were collected onto GF/C unifilter plates (Packard Instrument Co., Meriden, Conn.) using a Filtermate universal harvester and quantitated using a TopCount 96-well liquid scintillation counter (Packard Instrument Co., Meriden, Conn.). Compounds were dissolved in dimethylsulfoxide (DMSO) to a concentration of 10 mM and were evaluated at six concentrations diluted four-fold, each in triplicate. The final concentration of DMSO in the kinase assays was 0.5%, which was shown to have no effect on kinase activity. IC$_{50}$ values were derived by non-linear regression analysis and have a coefficient of variance (SD/mean, n=6)=10%.

The instant compounds inhibit VEGFR-2, FGFR-1 and PDGFR-β kinases with IC$_{50}$ values between 0.001–25 μM.

Methods of Preparation

The compounds of the present invention may be prepared by methods such as those illustrated in the following Schemes I to III. Solvents, temperatures, pressures, and other reaction conditions may readily be selected by one of ordinary skill in the art. Starting materials are commercially available or readily prepared by one of ordinary skill in the art.

Scheme 1

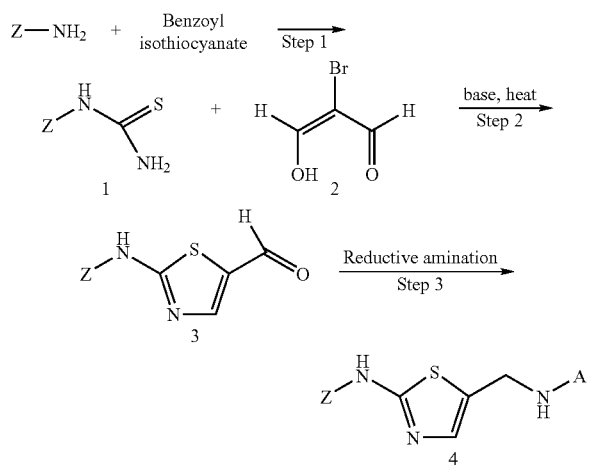

Step 1

An optionally substituted aniline is reacted with isothiocyanate such as benzoyl isothiocyanate in an organic solvents such as acetone preferably at elevated temperatures to afford thioureas of formula 1 of scheme 1.

Step 2

An optionally substituted thiourea, such as pyridylthiourea, can be reacted with 2-bromo-3-hydroxypropenal in the presence of a base, such as sodium acetate, to obtain a 2-aminothiazole carbaldehyde derivative 3 of scheme 1.

Step 3

The compound of formula 3 of scheme 1 can then be treated with an amine such as aniline in the presence of a reducing agent, such as sodium cyanoborohydride or triethylsilane in the presence of TFA, to form the compound of formula 4 of scheme 1.

Scheme 2

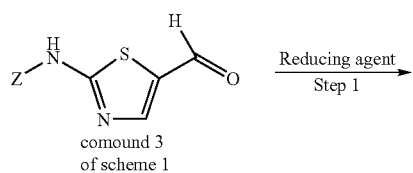

comound 3 of scheme 1

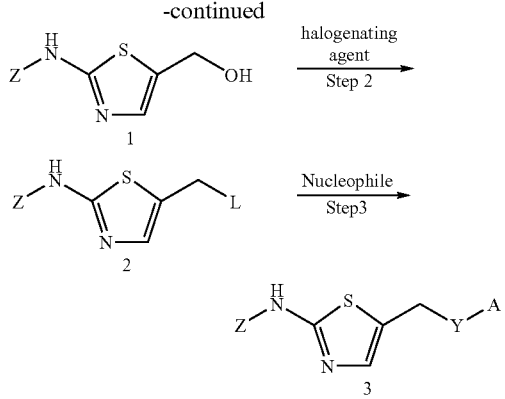

L = halogen

Step 1

A compound of formula 3 of scheme 1 can be reduced with a reducing agent, such potassium borohydride to obtain alcohol derivative compound 1 of scheme 2.

Step 2

A compound of formula 1 of scheme 2 then can be treated with halogenating agent such as thionyl chloride, to form the compound 2 of scheme 2.

Step 3

A compound of formula 2 of scheme 2 can then be alkylated with an nucleophiles, such as phenol, thiophenol or aniline to afford compound 3 of scheme 2.

Scheme 3

L = halogen

Step 1

An aryl or a heteroaryl halide such as 3-carboxy bromobenzene could be coupled with a borane derivative obtained from treatment of an alkene such as dialkoxybutene with a borane derivative such as 9-BBN in the presence of a catalyst such as palladium (0) followed by deprotection of a protecting group is any would afford an aldehyde of formula 1 of scheme 3.

Step 2

A compound of formula 1 of scheme 3 then can be treated with halogenating agent such as copper bromide, to form the compound 2 of scheme 3.

Step 3

A compound of formula 2 of scheme 3 then can be cyclized with an appropriate thiourea such as 1-(2-pyridyl)-2-thiourea, to obtain compound of formula 3 of scheme 3.

In addition, other compounds of formula I may be prepared using procedures generally known to those skilled in the art. In particular, the following examples provide additional methods for the preparation of the compounds of this invention.

The invention will now be further described by the following working example(s), which are preferred embodiments of the invention. All temperatures are in degrees Celsius (° C.) unless otherwise indicated. Preparative Reverse Phase (RP) HPLC purifications were done on C18 reverse phase (RP) columns using water/methanol mixtures with or without 0.1% TFA as buffer solution. All the synthesized compounds were characterized by at least proton NMR and LC/MS. During work up of reactions, the organic extract was dried over magnesium sulfate (MgSO$_4$), unless mentioned otherwise. The following abbreviations are used for the commonly used reagents; NMM; N-methylmorpholine, DIBAL; diisobutylaluminum hydride, BOP reagent; benzotriazol-1-yloxy-tris(trimethylamino)phosphonium hexafluorophosphate, DCE; dichloroethane, K$_2$CO$_3$; potassium carbonate, KOH; potassium hydroxide, DCC; dicyclohexyl carbodiimide, EDCI; 1-(dimethylaminopropyl)-3-ethylcarbodiimide hydrochloride, RT; room temperature, HOBt; hydroxybenzotriazole, DCM; dichloromethane, CbzCl; chlorobenzoyl chloride, NaHCO$_3$; sodium bicarbonate, HCl; hydrochloric acid, TFA; trifluoroacetic acid, NH$_4$Cl; ammonium chloride, DIPEA; diisopropylamine, Et$_3$N; triethylamine. Na$_2$SO$_4$; sodium sulfate, DEAD; diethyl azodicarboxylate, DPPA; diphenylphosphorylazide, DMF; dimethyl formamide, THF; tetrahydrofuran. EtOAc; ethyl acetate These examples are illustrative rather than limiting and it is to be understood that there may be other embodiments that fall within the spirit and scope of the invention as defined by the claims appended hereto.

EXAMPLE 1

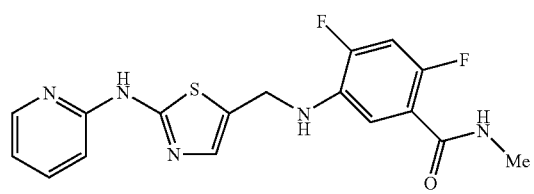

2,4Difluoro-N-methyl-5-{[2-(Pyridin-2-ylamino)-thiazole-5-ylmethyl]-amino}-benzamide Step A To a solution of 1-(2-pyridyl)-2-thiourea (765 mg, 5.0 mmol) in acetone (14 mL) was added slowly 2-bromo-3-hydroxypropenal (755 mg, 5.0 mmol, for preparation see J. Org. Chem. 28, 3243, 1963) in acetone (14 mL) over a period of 5 min. After stirring for 1.5 h, a precipitate formed. The solids were separated, washed with acetone (10 mL) and then taken into mixed solvent (ethanol/water=1/1, 9 mL). To this suspension was added sodium acetate (1.23 g, 15.0 mmol) and the resulting mixture was heated at 75° C. for 1 h. After cooling to RT, the mixture was filtered and the solids were washed with water (10 mL), and dried in vacuo to provide compound A, 2-(pyridin-2-ylamino)-thiazole-5-carbaldehyde (533 mg, 52%) as a solid. LC/MS; (M+H)$^+$=206

Step B

To a suspension of compound A (205 mg, 1.0 mmol) and 5-amino-2,4-difluoro-N-methyl-benzamide (186 mg, 1.0 mmol) in dichloromethane ( 9 mL) at RT was added trifluoroacetic acid (3 mL) and triethylsilane (232 mg, 2.0 mmol). The mixture was stirred at RT for 2 h and concentrated in vacuo. The residue was dissolved in dichloromethane, washed with sodium bicarbonate solution, dried and concentrated. The residue was purified by chromatography on silica gel eluting with 2% to 5% methanol in chloroform to provide the title compound, Example 1 (280 mg, 75%) as a light yellow solid. LC/MS; (M+H)$^+$=376.

The intermediate 5-amino-2,4-difluoro-N-methyl-benzamide was prepared as follows.

Step A

To a suspension of 2,4-difluorobenzoic acid (9.985 g, 63.2 mmol) in concentrated sulfuric acid (30 mL) at 0° C. was added fuming nitric acid (30 mL) over 30 min. The mixture was allowed to warm to RT and stirred for an additional 16 h. The homogeneous mixture was poured onto ice and extracted with ethyl acetate. The organic extract was washed with water, dried and concentrated in vacuo to afford 2,4-difluoro-5-nitrobenzoic acid (12.56 gm, 98%) as pale yellow solid.

Step B

To a solution of 2,4-difluoro-5-nitrobenzoic acid (0.998 g, 4.91 mmol) in ethanol (50 mL) was added 10% palladium on charcoal (107 mg) and the mixture was hydrogenated at 30 psi. After 2 h, the mixture was degassed, filtered and the filtrate was concentrated in vacuo to afford 2,4-difluoro-5-aminobenzoic acid (0.83 g, 97%) as tan solid. LC/MS (ESI); (M-H)$^-$=172.

Step C

To a solution of 2,4-difluoro-5-aminobenzoic acid (1.73 g, 10.0 mmol) in DMF (40 mL) were successively added EDCI (1.62 g, 12.0 mmol), HOBt (2.30 g, 12.0 mmol) and methylamine (6.0 mL, 12.0 mmol, 2 M in MeOH) in that order at RT. After stirring for 2 h, the reaction mixture was diluted with ethyl acetate (100 mL) and washed with water (100 mL). The aqueous layer was extracted with ethyl acetate (2×50 mL). The combined organic layer was washed with NaHCO$_3$ (3×50 mL) followed by 10% LiCl (50 mL). The organic layer was dried, filtered and concentrated to afford 5-amino-2,4-difluoro-N-methylbenzamide (0.76 g, 41%) as a light brownish solid. MS (M+H)$^+$=187. It was used without further purification (>92% pure by HPLC).

The following compounds were prepared using a procedure similar to that described for the preparation of Example 1. Substituent R is as defined in the following table.

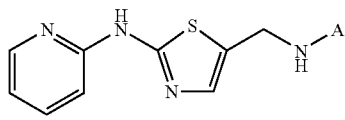

| Example # | A | Name | % yield | LC/MS; (M + H)+ |
|---|---|---|---|---|
| 2 | 4-F, 3-linked, C(O)NHMe | 4-Fluoro-N-methyl-3-{[2-(pyridin-2-ylamino)-thiazol-5-ylmethyl]-amino}-benzamide | 74 | 358 |
| 3 | 2-F, 5-linked, C(O)NHMe | 2-Fluoro-N-methyl-5-{[2-(pyridin-2-ylamino)-thiazol-5-ylmethyl]-amino}-benzamide | 39 | 358 |
| 4 | 4-Me, 3-linked, C(O)NHMe | 4,N-Dimethyl-3-{[2-(pyridin-2-ylamino)-thiazol-5-ylmethyl]-amino}-benzamide | 50 | 354 |
| 5 | 2-Me, 5-linked, C(O)NHMe | 2,N-Dimethyl-5-{[2-(pyridin-2-ylamino)-thiazol-5-ylmethyl]-amino}-benzamide | 62 | 354 |
| 6 | 4-F, 3-linked, C(O)NH-cyclopropyl | N-Cyclopropyl-4-fluoro-3-{[2-(pyridin-2-ylamino)-thiazol-5-ylmethyl]-amino}-benzamide | 81 | 384 |
| 7 | 4-CN, 3-linked, C(O)NH-cyclopropyl | 4-Cyano-N-cyclopropyl-3-{[2-(pyridin-2-ylamino)-thiazol-5-ylmethyl]-amino}-benzamide | 45 | 391 |
| 8 | 3-linked, COOH | 3-{[2-(Pyridin-2-ylamino)thiazol-5-ylmethyl]-amino}benzoic acid | 46 | 307 |

The anilines with N-methyl amides, required for the above examples, were prepared in a manner similar to the preparation of 5-amino-2,4-difluoro-N-methylbenzamide from commercially available benzoic acids.

5-amino-4-fluoro-methylbenzamide for Example 2 was prepared as follows.

Step A

A mixture of 3-nitro-4-fluorobenzoic acid (1.85 g, 10.0 mmol) in MeOH (10 mL) and 5% Pd/C (100 mg) was stirred under an atmosphere of hydrogen and for 6 h. The catalyst was removed by filtration, washed with methanol and the volatiles were removed in vacuo to give compound 8A, 3-amino-4-fluorobenzoic acid, as a light yellow solid (1.50 g, 9.67 mmol, 97%).

Step B

To a solution of 3-amino-4-fluorobenzoic acid (1.50 g, 9.67 mmol) in DMF (30 mL) were added successively EDCI (1.57 g, 11.6 mmol), HOBt (2.23 g, 11.6 mmol) and methylamine (5.8 mL, 11.6 mmol, 2M in MeOH). After stirring for 2 h at RT, the reaction mixture was diluted with ethyl acetate (100 mL), washed with water, NaHCO₃ (sat. 3×50 mL), and then 10% LiCl (50 mL). The organic layer was concentrated in vacuo to give the title compound (0.54 g, 3.20 mmol, 33%), as a brownish solid. LC/MS; (M+H)⁺=167 and was used without further purification (>91% pure by HPLC).

The aniline, 3-amino-4-cyano-N-cyclopropylbenzamide required for Example 7 was prepared by coupling 3-amino-4-cyanobenzoic acid with cyclopropyl amine in a manner similar to the procedure described for Example 2.

The compound of Example 6 can also be made by an alternative method.

To a mixture of 2-(pyridin-2-ylamino)-thiazol-5-carbaldehyde (41 mg, 0.2 mmol), 3-amino-4-fluoro-N-cyclopropylbenzamide (40.0 mg, 0.21 mmol) in TFA/DCM (1:1) (1 mL) was added triethylsilane (0.1 mL) at RT. The mixture was stirred for 1 h after addition. The mixture was concentrated and the residue was made alkaline with 2 N NaOH solution. The mixture was extracted with DCM (3×10 mL) and the extract was concentrated. The residue was purified by chromatography column (SiO2; ethyl acetate) to afford Example 6 as a solid, 62 mg (81%). MS: m/z 384 (M+H)⁺.

¹H NMR (DMSO-d6) δ 11.10 (s, 1 H), 8.27 ( d, J=5.0 Hz, 1 H), 8.23 (s, 1 H), 7.66 (m, 1 H), 7.29 (m, 1 H), 7.28 (s, 1 H), 7.03 (m, 3 H), 6.85 (m, 1 H), 6.22 (s, 1 H), 4.49 (d, J=7.65 Hz, 1 H), 2.78 (m, 1 H), 0.67 (m, 2 H), 0.54 (m, 2 H).

¹³C NMR (DMSO-d6) δ 167.1, 159.2, 152.6 (d, J=221.3 Hz), 151.8, 146.4, 137.9, 135.8 (d, J=10.1 Hz ), 135.1, 131.0, 127.6, 115.9, 115.4, 114.0 (d, J=10.1 Hz), 111.7, 110.8, 39.0, 23.1, 5.8.

EXAMPLE 9

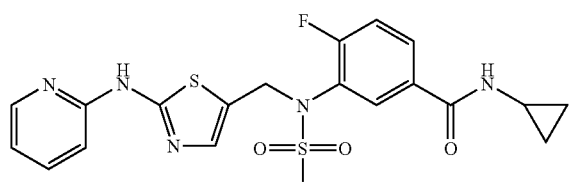

N-Cyclopropyl-4-fluoro-3-{methanesulfonyl-[2-(pyridin-2-ylamino)thiazol-5-ylmethyl]amino}-benzamide Step A To a solution of 2-(pyridin-2-ylamino)thiazole-5-carbaldehyde (410 mg, 2 mmol) in ethanol (15 mL) and DMF (5 mL) was added potassium borohydride (120 mg). The resulting mixture was stirred at RT for 1 h, quenched with 10% sulfuric acid solution and concentrated in vacuo. The residue was extracted with methanol and the methanol solution was concentrated. The crude material was diluted with water, filtered and the solid was washed with water and dried in vacuo to provide compound 9A, [2-(pyridin-2-ylamino)thiazol-5-yl]methanol (385 mg, 93%) as a solid. LC/MS; (M+H)⁺=208

Step B

A mixture of Compound 9A (20.7 mg, 0.1 mmol), N-cyclopropyl-4-fluoro-3-methanesulfonylaminobenzamide (326 mg, 0.12 mmol), triphenylphosphine (31.3 mg, 0.15 mmol) and DEAD (20 mg, 0.15 mmol) in THF (0.5 mL) was stirred at RT for 2 h and concentrated in vacuo. The residue was purified by chromatography on silica gel eluting with ethyl acetate and purified again by preparative HPLC. The appropriate fractions were collected, neutralized with sodium bicarbonate solution and lyophilized to afford N-cyclopropyl-4-fluoro-3-(methanesulfonyl-[2-(pyridin-2-ylamino)thiazol-5-ylmethyl]-amino}benzamide (12 mg, 26%) as a colorless solid. MS: [M+H]⁺=462.

N-cyclopropyl-4-fluoro-3-methanesulfonylaminobenzamide was prepared by treatment of N-cyclopropyl-4-fluoro-3-aminobenzamide (prepared by a procedure similar to Example 1) with methanesulfonyl chloride in the presence of pyridine by standard procedure.

EXAMPLE 10

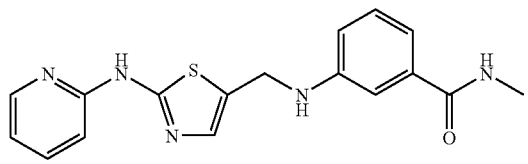

N-Methyl-3-{[2-(pyridin-2-ylamino)-thiazol-5-ylmethyl]-amino}benzamide

Step A

A mixture of [2-(pyridin-2-ylamino)thiazol-5-yl]methanol (414 mg, 2 mmol) and thionyl chloride (0.2 mL) in dichloromethane (25 mL) was stirred at 0° C. for 1 h and then concentrated in vacuo. The crude compound 10A, (5-chloromethyl-thiazol-2-yl)-pyridin-2-yl-amine (16 mg) was used directly for the next step.

Step B

A mixture of compound 10A (16 mg, 71 μmol) and 3-amino-N-methyl-benzamide (12 mg, 78 μmol) in DMF (0.7 mL) was stirred at RT for 2.5 h, diluted with 10% of lithium chloride solution and extracted with ethyl acetate (4×5 mL). The combined organic layer was washed with 10% lithium chloride solution, dried (Na₂SO₄) and concentrated. The residue was purified by chromatography on silica gel eluting with 2 to 5% methanol in chloroform to provide N-methyl-3-{[2-(pyridin-2-ylamino)thiazol-5-ylmethyl]amino}benzamide (2.5 mg, 10%). MS: [M+H]⁺=440.

EXAMPLE 11

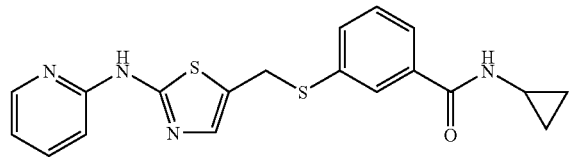

N-Cyclopropyl-3-[2-(pyridin-2-ylamino)-thiazol-5-ylmethylsulfanyl]-benzamide

Step A

A mixture of 3-mercaptobenzoic acid (308 mg, 2 mmol) and sodium hydride (60% in oil, 160 mg, 4 mmol) was stirred at RT under argon for 10 min and then cooled to 0° C. and (5-chloromethyl-thiazol-2-yl)pyridin-2-yl-amine hydrochloride salt (262 mg, 1 mmol) was added. The resulting reaction mixture was stirred at 0° C. for 1 h and acidified with 1N potassium hydrogen sulfate solution to pH=4. The mixture was filtered and the collected solid was washed with water and dried in vacuo to provide compound 11A, 3-[2-(pyridin-2-ylamino)thiazol-5-ylmethylsulfanyl] benzoic acid, which was used directly for the next step.

Step B

The crude compound 11A (~1 mmol) was dissolved in DMF (3 mL) and cyclopropylamine (0.2 mL, 4 mmol, excess), and BOP reagent (445 mg, 1 mmol) were added in that order. The mixture was stirred at RT for 1 h and then diluted with water. The solid was filtered, washed with water and dried in vacuo. The crude solid was recrystallized from ethyl acetate to afford the title compound (310 mg, 81%). MS: [M+H]$^+$=383.

EXAMPLE 12

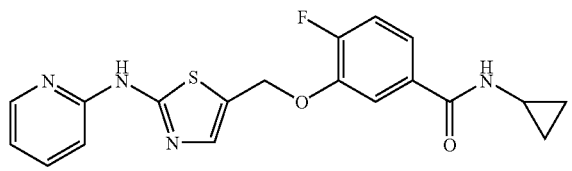

N-Cyclopropyl-4-fluoro-3-[2-(pyridin-2-ylamino)-thiazol-5-ylmethoxy]-benzamide

Step A

To a mixture of 3-hydroxy-4-fluorobenzoic acid (1.56 g, 10 mmol), cyclopropylamine (0.6 g, 10.5 mmol), triethylamine (1.02 g, 10 mmol) and HOBt (0.3 g, 2 mol) in DMF (10 mL) was added EDCI (2.0 g, 10.5 mmol) at RT. The mixture was stirred at RT overnight. The mixture was diluted with water and extracted with ethyl acetate (3×20 mL). The extract was washed with water and concentrated to afford 3-hydroxy-4-fluoro-N-cyclopropylbenzamide as a solid (1.2 g, 61.5%).

Step B

To a suspension of NaR (16 mg, 60% in oil) in DMF (1 mL) was added a solution of 3-hydroxy-4-fluoro-N-cyclopropylbenzamide (58.5 mg, 0.3 mmol) in DMF (1 mL) at RT. After 10 min, (5-chloromethylthiazol-2-yl)pyridin-2-ylamine hydrochloride (Example 10A) (52.4 mg, 0.2 mmol) was added. The mixture was stirred at RT for 1 h and poured onto ice. The mixture was neutralized with 1 N KHSO4 solution and the precipitates were collected, washed with water and ethyl acetate to give the title compound as a light yellow solid (25.2 mg, 33%). MS m/z 385 (M+H)$^+$.

EXAMPLE 13

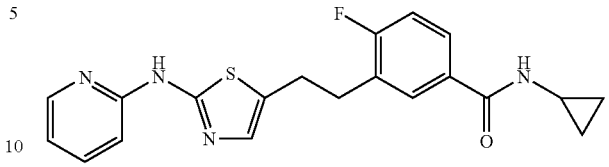

N-Cyclopropyl-4-fluoro-3-{2-[2-(pyridin-2-ylamino)-thiazol-5-yl]-ethyl}-benzamide Step A A solution of 3-butenal diethyl acetal (144 mg, 1 mmol) and 9-BBN (0.5 M in THF, 2.2 mL, 1.1 mmol) was stirred at RT for 1 h. The mixture was concentrated and to the residue were added benzene (2 mL), EtOH (1 mL), aqueous Na$_2$CO$_3$ solution (2M, 1 mL), 3-bromo-4-fluoro-N-cyclopropylbenzamide (127 mg, 0.5 mmol) and Pd(Ph$_3$P)$_4$ (40 mg). The resulting mixture was stirred at 80° C. for 2 h. The mixture was then cooled to RT and diluted with ethyl acetate (10 mL) and washed with water. The organic layer was separated and concentrated. The residue was purified by column chromatography (SiO$_2$; EtOAc/hexane 1:3) to afford N-cyclopropyl-3-(4,4-diethoxybutyl)-4-fluorobenzamide (151 mg, 93%). This material was dissolved in acetone (1 mL) and 3 N HCl solution (0.2 mL) and stirred at RT for 1 h. The mixture was neutralized with NaHCO$_3$ solution and extracted with ethyl acetate (3×5 mL). The organic layer was dried and concentrated to afford N-cyclopropyl-4-fluoro-3-(4-oxo-butyl)-benzamide (110 mg, 94%).

$^1$H NMR (CDCl$_3$) δ 9.76 (s, 1 H), 7.63 (dd, 1 H, J=7.5 and 2.2 Hz,), 7.58 (m, 1 H), 7.03 (t, 1 H, J=9.0 Hz,), 6.47 (s, NH, 1 H), 2.87 (m, 1 H), 2.69 (t, 2 H, J=7.5 Hz,), 2.48 (m, 2 H), 1.95 (m, 2 H), 0.86 (m, 2 H) and 0.62 (m, 2 H).

Step B

A solution of the above compound (110 mg, 0.44 mmol) and CuBr$_2$ (148 mg, 0.66 mmol) in acetonitrile (1 mL) were stirred at RT for 4 h. The mixture was diluted with ethyl acetate (10 mL), washed with brine, concentrated and the residue was dissolved in acetic acid (0.5 mL). Sodium acetate (100 mg) and N-pyridyl thiourea (67 mg, 0.5 mmol) were added and the mixture was stirred at 100° C. for 1 h. The volatiles were removed and the residue was neutralized with NaHCO$_3$ solution and extracted with ethyl acetate (3×10 mL). The organic extract was concentrated and the residue was purified by column chromatograph (SiO$_2$, EtOAc/hexanes 1:1) to afford the title compound (17.0 mg, 10%). MS m/z 383 (M+H)$^+$.

$^1$H NMR (DMSO-d6) δ 11.03 (s, 1 H), 8.40 (d, 1 H, J=4 Hz,), 8.24 (d, 1H, J=5 Hz), 7.84 (m, 1 H), 7.73 (m, 1 H), 7.66 (t,1 H, J=7.8 Hz), 7.22 (t, 1 H, J=7.8 Hz,), 7.04 (s, 1 H), 7.03 (d, 1 H, J=8.0 Hz), 6.88 (m, 1 H), 3.01 (t, 2 H, J=7.5 Hz), 2.95 (t, 2 H, J=7.5 Hz), 2.83 (m, 1 H), 0.68 (m, 2 H), 0.56 (m, 2 H).

EXAMPLE 14

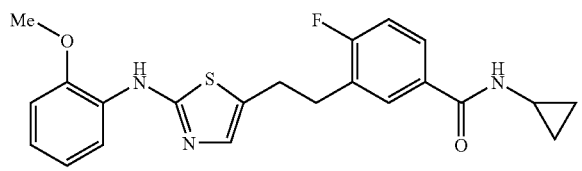

N-Cyclopropyl-4-fluoro-3-{2-[2-(2-methoxy-phenylamino)-thiazol-5-yl]-ethyl}-benzamide Compound 14 is prepared in a manner similar to the preparation of example 13 by using the appropriate thiourea. For the preparation of thiourea, see Example 16. LC/MS; (M+H)+=412

EXAMPLE 15

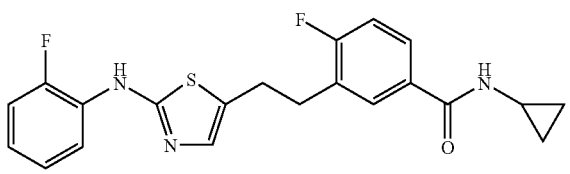

N-Cyclopropyl-4-fluoro-3-{2-[2-(2-fluoro-phenylamino)-thiazol-5-yl]-ethyl}-benzamide Compound 15 is prepared in a manner similar to the preparation of example 13 by using the appropriate thiourea. For the preparation of the thiourea, see Example 16. LC/MS; (M+H)==400.

EXAMPLE 16

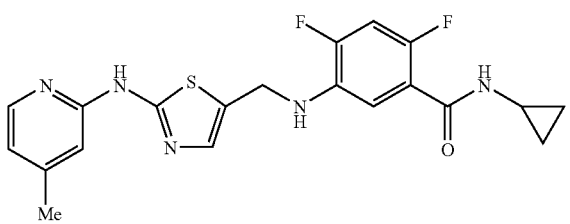

N-Cyclopropyl-2,4-difluoro-5-{[2-(4-methyl-pyridin-2-ylamino)-thiazol-5-ylmethyl]-amino}-benzamide Step A A solution of 2-amino-4-methylpyridine (1.08 g, 10 mmol) and benzoyl isothiocyanate (1.63 g, 10 mmol) in acetone (15 mL) was stirred at RT for 1.5 h. The precipitate formed was filtered and washed with acetone to afford 1-benzoyl-3-[4-methylpyridin-2-yl]-thiourea as a solid. This material was stirred with 2 N NaOH solution (15 mL) at 110° C. for 1 h, then cooled to RT, and the precipitate formed was washed with water and dried to provide (4-methylpyridin-2-yl)-thiourea (0.90 g, 53%). MS m/z 168 (M+H)+.

Step B

A mixture of (4-methylpyridin-2-yl)-thiourea (334 mg, 2 mmol), 2-bromomalonaldehyde (302 mg, 2 mmol) and sodium acetate (250 mg, 3.0 mmol) in acetic acid (5 mL) was stirred at 100° C. for 3 h. The mixture was cooled to RT and diluted with water and the precipitate formed was collected, washed with water and dried to afford 2-(4-methylpyridin-2-ylamino)-thiazole-5-carbaldehyde (350 mg, 80%). MS m/z 220 (M+H)+.

Step C 2-(4-Methylpyridin-2-ylamino)-thiazole-5-carbaldehyde was treated with 5-amino-N-cyclopropyl-2,4-difluorobenzamide (for preparation see Example 18) in a manner similar to Example 1 to afford the title compound. LC/MS; (M+H)+= 416.

EXAMPLE 17

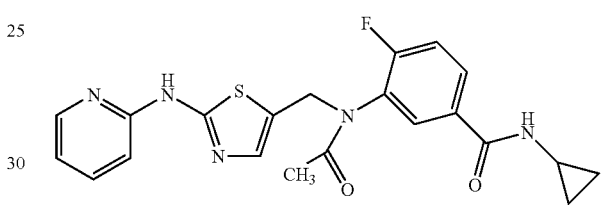

3-{Acetyl-[2-(pyridin-2-ylamino)-thiazol-5-ylmethyl]-amino}-N-cyclopropyl-4-fluorobenzamide To a mixture of Example 6 (16.5 mg, 0.043 mol) in pyridine (0.3 mL) at RT was added acetic anhydride (10 mg, 0.1 mmol). After stirring at RT for 1 h the solvent was removed and the residue was diluted with water. The precipitate formed was filtered, washed with water and dried in vacuo to afford the title compound (11 mg, 60%). MS m/z 426 (M+H)+.

EXAMPLE 18

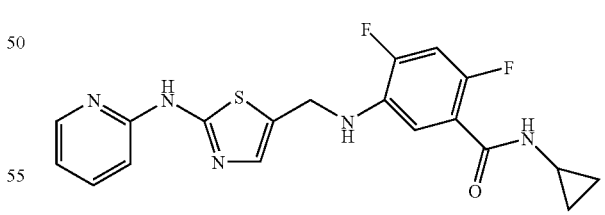

N-Cyclopropyl-2,4-difluoro-5-{[2-(pyridin-2-ylamino)-thiazol-5-ylmethyl]-amino}-benzamide Step A 2,4-difluoro-5-nitrobenzoic acid (2.03 g, 10 mmol, see example 1) was refluxed in thionyl chloride (10 mL) for 3 h. The mixture was cooled, concentrated and the residue was dissolved in DCM (20 mL). The mixture was cooled to −40°

C. and cyclopropylamine (0.57 mg, 10 mmol) and triethylamine (2.02 g, 20 mmol) were added. The mixture was stirred at 40° C. for 1 h, warmed to RT, and acidified with 1 N HCl solution (10 mL). The DCM layer was separated, washed with 1 N HCl solution followed by NaHCO$_3$ solution, then dried, and concentrated to afford N-cyclppropyl-2,4-difluoro-5-nitrobenzamide as a solid (1.95 g, 80%).

$^1$H NMR (CDCl$_3$) δ 8.93 (t,1 H, J=7.75 Hz), 7.11 (t, 1 H, J=7.75 Hz), 6.68 (s, 1H), 2.95 (m, 1 H), 0.93 (m, 2 H), 0.66 (m, 2 H).

Step B

A mixture of the above nitro compound (1 g, 4.1 mmol) and Pd/C (10%, 0.1 g) in ethyl acetate/ethanol (1:1, 15 mL) mixture was hydrogenated under hydrogen atmosphere for 2 h. The mixture was filtered and concentrated to afford 5-amino-N-cyclopropyl-2,4-difluorobenzamide as a solid, 0.85 g (97%). MS m/z 213 (M+H)$^+$.

$^1$H NMR (CDCl$_3$) δ 7.53 (t, 1 H, J=7.75 Hz), 6.80 (t, 1 H, J=7.75 Hz), 3.74 (s, 2 H). 2.91 (m, 1 H), 0.87 (m, 2 H), 0.61 (m, 2 H).

Step C

A mixture of 2-[pyridin-2-ylamino]-thiazole-5-carbaldehyde (41.0 mg, 0.2 mmol) and 5-amino-N-cyclopropyl-2,4-difluorobenzamide (46.6 mg, 0.22 mmol) in TFA/DCM (1:1, 1 mL) was stirred at RT for 10 min and triethylsilane (0.1 mL) was added. The mixture was stirred for 1 h, then concentrated and the residue was neutralized with NaHCO$_3$ solution and the precipitates occurred. The precipitates were collected, washed with water and dried. The solid was triturated with MeOH and filtered to afford the title compound as a grayish solid (38 mg, 47%). Small amount of solid was boiled in methanol, the mixture was cooled to RT and filtered to afford a white solid. MS m/z 402 (M+H)$^+$. $^1$H NMR (DMSO-d6) δ 8.23 (d, 1H, J=4.0 Hz), 8.15 (s, 1 H), 7.65 (t, 1 H, J=7.15 Hz), 7.26 (s, 1 H), 7.16 (m, 1 H), 7.01 (d, 1 H, J=8.75 Hz), 6.95 (m, 1 H), 6.89 (t, 1 H, J=7.15 Hz), 6.12 (s 1 H), 4.43 (m, 2 H), 2.79 (m, 1 H), 0.69 (m, 2 H), 0.51 (m, 2 H).

EXAMPLE 19

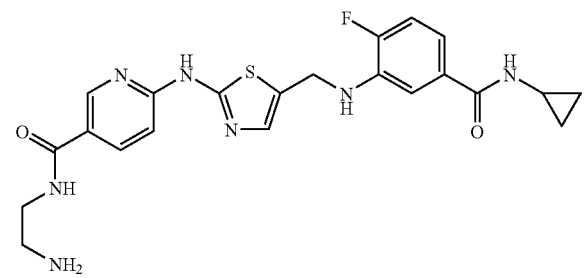

N-(2-Amino-ethyl)-6-{5-[(5-cyclopropylcarbamoyl-2-fluoro-phenylamino)-methyl]-thiazol-2-ylamino}-nicotinamide Step A A solution of ethyl 6-amino-nicotinate (830 mg, 5 mmol) and benzoyl isothiocyanate (830 mg, 5.1 mmol) in acetone was refluxed for 2 h. The mixture was concentrated to thin slurry and methanol was added. The solid was filtered, washed with methanol and dried to afford ethyl 6-(3-benzoyl-thioureido)-nicotinate (1.35 g, 82%). $^1$H NMR (CDCl$_3$) δ 13.34 (s, 1 H), 9.04 (m, 3 H), 8.38 (s, 1 H), 7.93 (m, 2 H), 7.66 (m, 3 H), 4.42 (q, 2 H, J=7.6 Hz), 1.41(t, 3 H, J=7.6 Hz).

This material was suspended in 2 N NaOH solution (5 mL) and refluxed for 1 h. The mixture was cooled to RT and acidified with 1 N HCl solution to pH 4. The solid was collected, washed with water followed by methanol and dried in vacuo to afford 6-thioureido-nicotinic acid (0.64 g, 79%). MS m/z 198 (M+H)$^+$.

Step B

A mixture of 6-thioureido-nicotinic acid (197 mg, 1 mmol), 2-bromomalonaldehyde (166 mg, 1.1 mmol) and sodium acetate (100 mg) in acetic acid (2 mL) was stirred at 100° C. for 20 min. The mixture was then cooled to RT, diluted with water and the precipitates were collected. The solid was washed with water, then methanol and dried in vacuo to afford 6-(5-formyl-thiazol-2-ylamino)-nicotinic acid, (240 mg, 96%). MS m/z 250 (M+H)$^+$. $^1$H NMR (DMSO-d6) δ 12.7 (s, 1 H), 9.12 (s, 1 H), 8.92 (s, 1 H), 8.38 (s, 1 H), 8.24 (d, 1 H, J=5.6 Hz), 7.21 (d, 1 H, J=5.6 Hz). $^{13}$C NMR (DMSO-d6) δ 183.5, 166.0, 165.1, 153.3, 151.5, 148.8, 139.1, 131.2, 120.3, 110.0.

Step C

The above compound 19B was treated with 3-amino-4-fluoro-N-cyclopropylbenzamide as described in the preparation of Example 6 to afford 6-{5-[(5-cyclopropylcarbamoyl-2-fluoro-phenylamino)-methyl]-thiazol-2-ylamino}-nicotinic acid (86% yield). MS m/z 428 (M+H)$^+$. $^1$H NMR (DMSO-d6) δ 11.37 (s, 1 H), 8.95 (s, 1 H), 8.47 (s, 1 H), 8.24 (d, 1 H, J=7.5 Hz), 7.37 (s, 1 H), 7.26 (d, 1 H, J=7.5 Hz), 7.12 (m, 2 H), 4.61(s, 2 H), 2.72 (m, 1 H), 0.69 (m, 2 H), 0.59 (m, 2 H).

Step D

To a solution of the above compound 19 C (42.7 mg, 0.1 mmol), triethylamine (20 mg), and N-tert-butoxycarbonyl-ethyldiamine (35.2 mg, 0.22 mmol) in DMF (0.3 mL) at RT, was added BOP reagent (50 mg, 0.11 mmol). After stirring at RT for 0.5 h the mixture was diluted with water and the solid was collected, washed with water and dried in vacuo. The solid was dissolved in TFA/DCM (1:1, 0.5 mL) and stirred at RT for 0.5 h. The solvent was removed and the residue was adjusted to pH 10 with NaOH solution. The solid was collected, washed with water and dried in vacuo. The material was converted to HCl salt by adding MeOH—HCl (28 mg, 55%). MS: m/z 470 (M+H)$^+$.

EXAMPLE 20

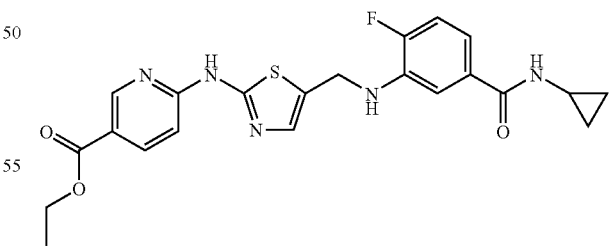

6-{5-[(5-Cyclopropylcarbamoyl-2-fluoro-phenylamino)-methyl]-thiazol-2-ylamino}-nicotinic acid ethyl ester Step A A solution of ethyl 6-amino-nicotinate (10.7 g, 64.5 mmol) and N—Fmoc isothiocyanate (19.0 g, 67.7 mmol) in THF (100 mL) was refluxed for 2 h and the most of THF was removed. The residue was triturated with DCM (50 mL) and hexanes (200 mL), and the solid was collected. The solid was washed with 20% DCM in hexanes and dried to afford ethyl 6-(3-Fmoc-thioureido)-nicotinate, 28.5 g (99%). This material was dissolved in DCM (200 mL) and stirred with pyrrolidine (5.5 g, 77.5 mmol) at RT for 3 h. The solid was collected and washed with DCM to afford ethyl 6-thioureido-nicotinate (13.2 g, 94%). MS m/z 226 (M+H)⁺.

Step B

The above compound 20A was treated with 3-amino-4-fluoro-N-cyclopropylbenzamide as described in the preparation of Example 6 to afford the title compound. LC/MS; (M+H)⁺=456.5

EXAMPLE 21

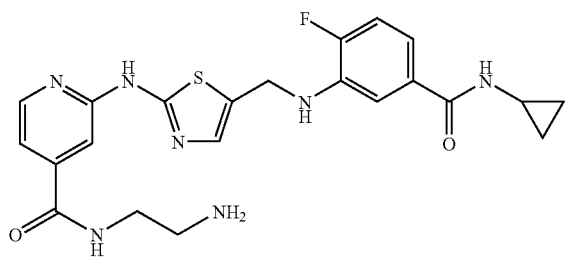

N-(2-Amino-ethyl)-2-{5-[(5-cyclopropylcarbamoyl-2-fluoro-phenylamino)-methyl]-thiazol-2-ylamino}-isonicotinamide Compound 21 was prepared in a manner similar to the preparation of Example 19 using 2-amino-isonicotinic acid instead of ethyl-6-aminonicotinic acid. LC/MS; (M+H)⁺= 470.

EXAMPLE 22

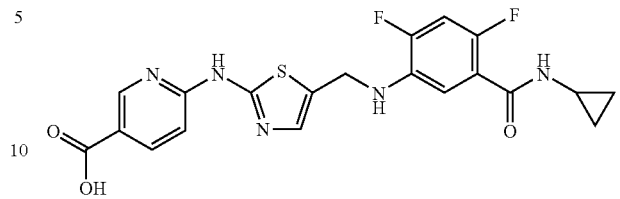

6-{5-[(5-Cyclopropylcarbomoyl-2,4-difluoro-phenylamino)-methyl]-thiazol-2-ylamino}-nicotinic acid 6-(5-Formyl-thiazol-2-ylamino)-nicotinic acid (see Example 19) was treated with 5-amino-2,4-difluoro-N-cyclopropylbenzamide in manner similar to the preparation of Example 6 to afford the title compound in 95% yield. LC/MS; (M+H)⁺=446

EXAMPLE 23

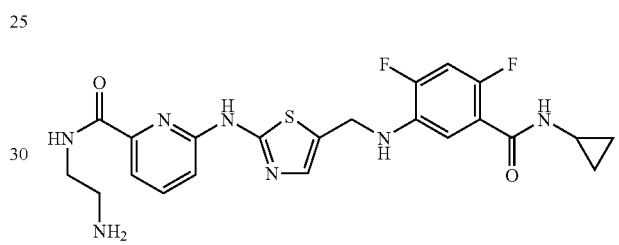

6-{5-[(5-Cyclopropylcarbamoyl-2,4-difluoro-phenylamino)-methyl]-thiazol-2-ylamino}-pyridine-2-carboxylic acid (2-aminoethyl)-amide The title compound was prepared in a manner similar to the preparation of Example 19 using 6-aminopyridine-2-carboxylic acid instead of ethyl-6-aminonicotinic acid. Yield 42%. LC/MS; (M+H)⁺=488

The following compounds were prepared from Example 22 by coupling with an appropriate amine utilizing procedure 19D described above for the preparation Example 19.

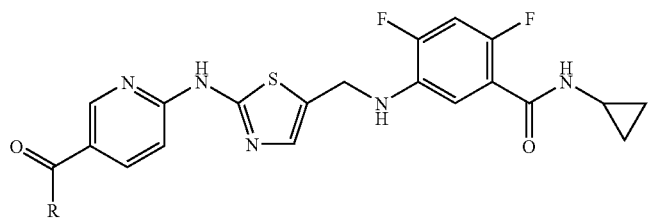

| Example # | R | Name | % yield | LC/MS; (M + H)⁺ |
|---|---|---|---|---|
| 24 | ![NH-CH2CH2-NH2] | N-(2-Amino-ethyl)-6-{5-[(5-cyclopropylcarbamoyl-2,4-difluoro-phenylamino)-methyl]-thiazol-2-ylamino}-nicotinamide | 23 | 488 |

-continued

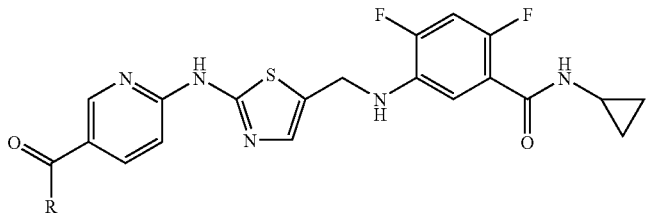

| Example # | R | Name | % yield | LC/MS; (M + H)+ |
|---|---|---|---|---|
| 25 | -N(Me)CH2CH2NH2 | N-(2-Amino-ethyl)-6-{5-[(5-cyclopropylcarbamoyl-2,4-difluoro-phenylamino)-methyl]-thiazol-2-ylamino}-N-methyl-nicotinamide | 7 | 502 |
| 26 | -NHCH2CH2NHMe | 6-{5-[(5-Cyclopropylcarbamoyl-2,4-difluoro-phenylamino)-methyl]-thiazol-2-ylamino}-N-(2-methylaminoethyl)-nicotinamide | 13 | 502 |
| 27 | -NHCH2CH2NHEt | 6-{5-[(5-Cyclopropylcarbamoyl-2,4-difluoro-phenylamino)-methyl]-thiazol-2-ylamino}-N-(2-ethylaminoethyl)-nicotinamide | 79 | 516 |
| 28 | piperazin-1-yl | N-Cyclopropyl-2,4-difluoro-5-({2-[5-(piperazine-1-carbonyl)-pyridin-2-ylamino]-thiazol-5-ylmethyl}-amino)-benzamide | 50 | 514 |
| 29 | -N(Me)CH2CH2NHMe | 6-{5-[(5-Cyclopropylcarbamoyl-2,4-difluoro-phenylamino)-methyl]-thiazol-2-ylamino}-N-methyl-N-(2-methylaminoethyl)-nicotinamide | 46 | 516 |
| 30 | -NHCH2C(Me)2NH2 | N-(2-Amino-2-methyl-propyl)-6-{5-[(5-cyclopropylcarbamoyl-2,4-difluoro-phenylamino)-methyl]-thiazol-2-ylamino}-nicotinamide | 72 | 516 |
| 31 | 4-methylpiperazin-1-yl | N-Cyclopropyl-2,4-difluoro-5-({2-[5-(4-methyl-piperazine-1-carbonyl)-pyridin-2-ylamino]-thiazol-5-ylmethyl}-amino)-benzamide | 85 | 528 |
| 32 | -NH-(piperidin-4-yl) | 6-{5-[(5-Cyclopropylcarbamoyl-2,4-difluoro-phenylamino)-methyl]-thiazol-2-ylamino}-N-piperidine-4-yl-nicotinamide | 95 | 528 |
| 33 | -N(Me)CH2CH2NMe2 | 6-{5-[(5-Cyclopropylcarbamoyl-2,4-difluoro-phenylamino)-methyl]-thiazol-2-ylamino}-N-(2-dimethylamino-ethyl)-N-methylnicotinamide | 45 | 530 |
| 34 | 3-aminopyrrolidin-1-yl | 5-({2-[5-(3-Amino-pyrrolidine-1-carbonyl)-pyridin-2-ylamino]-thiazol-5-ylmethyl}-amino)-N-cyclopropyl-2,4-difluorobenzamide | 81 | 514 |

-continued

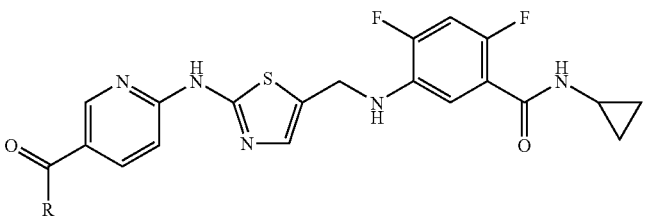

| Example # | R | Name | % yield | LC/MS; (M + H)+ |
|---|---|---|---|---|
| 35 | (3-amino-pyrrolidin-1-yl) | 5-({2-[5-(3-Amino-pyrrolidine-1-carbonyl)-pyridin-2-ylamino]-thiazol-5-ylmethyl}-amino)-N-cyclopropyl-2,4-difluorobenzamide | 71 | 514 |

The following compounds were prepared in a manner similar to the procedure described for the preparation of Example 16 using an appropriate aminopyridine or aniline.

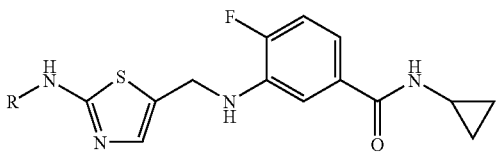

| Example # | R | Name | % yield | LC/MS; (M + H)+ | Name | % yield | LC/MS; (M + H)+ |
|---|---|---|---|---|---|---|---|
| 36 | 6-methyl-pyridin-2-yl | N-Cyclopropyl-4-fluoro-3-{[2-(6-methyl-pyridin-2-ylamino)-thiazol-5-ylmethyl]-amino}-benzamide | 30 | 398 | | | |
| 37 | pyridin-3-yl | N-Cyclopropyl-4-fluoro-3-{[2-(pyridin-3-ylamino)-thiazol-5-ylmethyl]-amino}-benzamide | 46 | 384 | N-Cyclopropyl-4-fluoro-3-{[2-(pyrimidin-2-ylamino)-thiazol-5-ylmethyl]-amino}-benzamide | 63 | 385 |
| 39 | 4-methyl-pyrimidin-2-yl | N-Cyclopropyl-4-fluoro-3-{[2-(4-methyl-pyrimidin-2-ylamino)-thiazol-5-ylmethyl]-amino}-benzamide | 49 | 399 | | | |

-continued

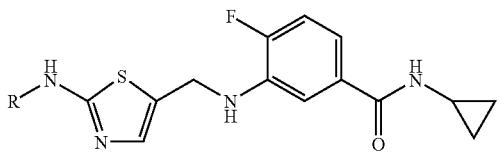

| Example # | R | Name | % yield | LC/MS; (M + H)+ |
|---|---|---|---|---|
| 40 | quinolin-2-yl | N-Cyclopropyl-4-fluoro-3-{[2-(quinolin-2-ylamino)-thiazol-5-ylmethyl]-amino}-benzamide | 56 | 434 |
| 41 | 5-cyanopyridin-2-yl | 3-{[2-(5-Cyano-pyridin-2-ylamino)-thiazol-5-ylmethyl]-amino}-N-cyclopropyl-4-fluorobenzamide | 69 | 412 |
| 42 | 2-nitrophenyl | N-Cyclopropyl-4-fluoro-3-{[2-(2-nitro-phenylamino)-thiazol-5-ylmethyl]-amino}-benzamide | 71 | 428 |

EXAMPLE 43

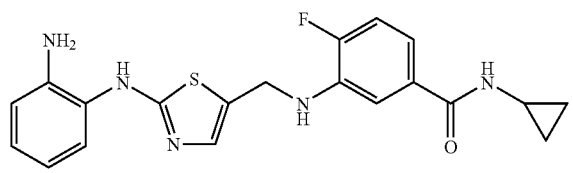

3-{[2-(2-Amino-phenylamino)-thiazol-5-ylmethyl]-amino}-N-cyclopropyl-4-fluoro-benzamide To a suspension of Example 42 (26 mg, 0.06 mmol) and Raney/Ni (26 mg) in THF (1.5 ml) at RT, hydrazine (0.5 ml) was added. The above reaction mixture was heated to 60° C. for 30 minutes, cooled to RT, filtered, and rinsed with EtOAc. The filtrate was dried over $Na_2SO_4$, concentrated, and purified by silica gel eluted with 5–12% $MeOH/CHCl_3$ to give 3-{[2-(2-amino-phenylamino)-thiazol-5-ylmethyl]-amino}-N-cyclopropyl-4-fluorobenzamide as a light yellow solid (6 mg, 25%). $(M+H)^+=398$.

The following compounds were prepared in a manner similar to the procedure described for the preparation of Example 16 using an appropriate aniline.

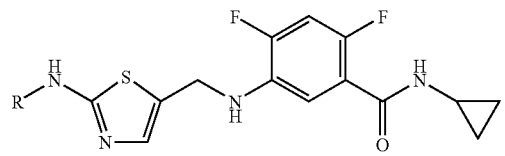

| Example # | R | Name | % yield | LC/MS; (M + H)+ |
|---|---|---|---|---|
| 44 | quinolin-2-yl | N-Cyclopropyl-2,4-difluoro-5-{[2-(quinolin-2-ylamino)-thiazol-5-ylmethyl]-amino}-benzamide | 69 | 452 |
| 45 | 6-bromopyridin-2-yl | 5-{[2-(6-Bromopyridin-2-ylamino)-thiazol-5-ylmethyl]-amino}-N-cyclopropyl-2,4-difluorobenzamide | 68 | 481 |
| 46 | 6-(4-methylpiperazin-1-yl)-pyridin-2-yl | N-Cyclopropyl-2,4-difluoro-5-({2-[6-(4-methylpiperazin-1-yl)-pyridin-2-ylamino]-thiazol-5-ylmethyl}-amino)-benzamide | 50 | 500 |
| 47 | 5-bromopyridin-2-yl | 5-{[2-(5-Bromopyridin-2-ylamino)-thiazol-5-ylmethyl]-amino}-N-cyclopropyl-2,4-difluorobenzamide | 94 | 481 |

EXAMPLE 48

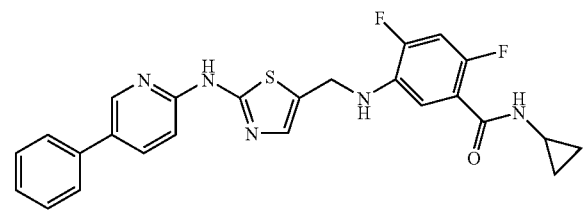

N-Cyclopropyl-2,4-difluoro-5-{[2-(5-phenyl-pyridin-2-ylamino)-thiazol-5-ylmethyl]-amino}-benzamide A mixture of Example 47 (96 mg, 0.20 mmol), phenyl boronic acid (31 mg, 0.3 mmol), tetrakis(triphenyl)phosphine palladium (4 mg) and aqueous 2M $K_2CO_3$ in toluene/ EtOH (1 mL/1 mL) mixture was degassed 3 times and flushed with argon. The reaction mixture was heated to 80° C. overnight. After cooling to RT, the mixture was diluted with dichloromethane (5 mL) and washed with water (2×5 mL). The organic layer was dried over $Na_2SO_4$, concentrated, and purified by silica gel eluted with 1–3% MeOH/ $CHCl_3$ to afford the title compound as a light yellow solid (40 mg, 40%). $(M+H)^+=478$ Examples 49 and 50 were prepared from Example 47 in a manner similar to the preparation of Example 48. Example 51 was prepared from Example 45 in a manner similar to the preparation of Example 48

| Example # | R | Name | % yield | LC/MS; (M + H)+ |
|---|---|---|---|---|
| 49 | (3-pyridyl-pyridyl group) | 5-{[2-([3,3']Bipyridinyl-6-ylamino)-thiazol-5-ylmethyl]-amino}-N-cyclopropyl-2,4-difluoro-benzamide | 15 | 479 |
| 50 | (4-aminomethylphenyl-pyridyl group) | 5-({2-[5-(4-Aminomethyl-phenyl)-pyridin-2-ylamino]-thiazol-5-ylmethyl}-amino)-N-cyclopropyl-2,4-difluoro-benzamide | 10 | 507 |
| 51 | ([2,3']bipyridinyl group) | 5-{[2-([2,3']Bipyridinyl-6-ylamino)-thiazol-5-ylmethyl]-amino}-N-cyclopropyl-2,4-difluoro-benzamide | 15 | 479 |

EXAMPLE 52

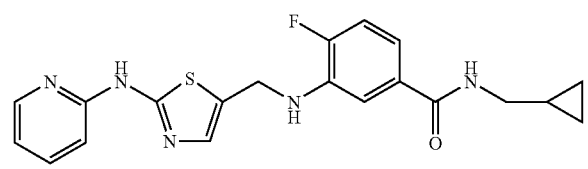

N-Cyclopropylmethyl-4-fluoro-3-{[2-(pyridin-2-ylamino)-thiazol-5-ylmethyl]-amino}-benzamide Step A To a suspension of 2-(pyridin-2-ylamino)-thiazole-5-carbaldehyde (1.0 g, 4.90 mmol, compound 1A) in methylene chloride (20 mL) at RT 3-amino-4-fluorobenzoic acid (0.95 g, 4.90 mmol) TFA (5 mL) and triethylsilane (1.71 mg, 14.7 mmol) were added. The above reaction mixture was stirred at RT for 4 h, then concentrated in vacuo and the resulting slurry was triturated with methanol to afford 4-fluoro-3-{[2-(pyridin-2-ylamino)-thiazol-5-ylmethyl]-amino}-benzoic acid as light yellow solid (1.54 g, 91%) (M+H)+=345.

Step B

To a solution of 4-fluoro-3-{[2-(pyridin-2-ylamino)-thiazol-5-ylmethyl]-amino}-benzoic acid (35 mg, 0.10 mmol) in DMF (1 mL) at RT, cyclopropylmethyl amine (14 mg 0.20 mmol) was added followed by the addition of BOP reagent (53 mg, 0.12 mmol). The above reaction mixture was stirred for 2 h, diluted with EtOAc (10 mL), washed with 10% NaHCO$_3$ (3×5 mL), and 10% LiCl (5 mL). The organic layer was dried over Na$_2$SO$_4$, concentrated and the residue was purified by preparative HPLC to give the title compound as a off-white solid (33 mg, 83%). (M+H)+=398.

EXAMPLE 53

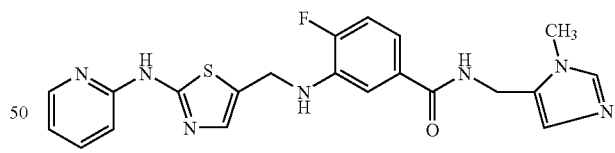

4-Fluoro-N-(3-methyl-3H-imidazol-4-ylmethyl)-3-{[2-(pyridin-2-ylamino)-thiazol-5-ylmethyl]-amino}-benzamide To a solution of compound 52A (68.8 mg, 0.2 mmol) and 5-aminomethyl-1-methylimidazole 2 HCl salt (40.0 mg, 0.22 mmol) in pyridine (0.5 mL) was added triethylamine (50 mg, 0.5 mmol) and BOP reagent (100 mg, 0.23 mmol). After stirring at RT for 2 h, the mixture was concentrated and the residue was diluted with water. The solid was collected, washed with water, MeOH and dried to afford the title compound (70 mg, 80%). MS m/z 438(M+H)+.

EXAMPLE 54

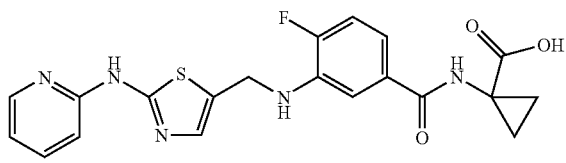

1-(4-Fluoro-3-{[2-(pyridin-2-ylamino)-thiazol-5-ylmethyl]-amino}-benzoylamino)-cyclopropanecarboxylic acid Step A Compound 52 A was treated with 1-amino-cyclopropanecarboxylic acid ethyl ester in a manner similar to the preparation of Example 53 to afford 1-(4-fluoro-3-{[2-(pyridin-2-ylamino)-thiazol-5-ylmethyl]-amino}-benzoylamino)-cyclopropanecarboxylic acid ethyl ester in 95% yield. LC/MS; (M+H)$^+$=456.

Step B

A solution of the above compound 54A (455 mg, 1 mmol) and 2N NaOH (5 mL) in ethanol (10 mL) was refluxed for 2 h. After cooling to RT, the mixture was acidified with 1 N HCl solution and the solid was collected, washed with water and dried to afford 1-(4-fluoro-3-{[2-(pyridin-2-ylamino)-thiazol-5-ylmethyl]-amino}-benzoylamino)-cyclopropanecarboxylic acid (167 mg, 39%). MS m/z 428 (M+H)$^+$.

To a solution of N—Fmoc aminocyclopropylcarboxylic acid (2.00 g, 6.19 mmol)in DCM (20 mL) and DMF (0.5 mL) was added a solution of oxalyl chloride (2 M in DCM, 10 mL) at RT. The mixture was stirred for 4 h. The mixture was concentrated and the residue was dissolved in THF (15 ml) and NaBH4 (470 mg, 12.4 mmol) was added. The mixture was refluxed for 2 h and poured onto ice. The solid was collected, washed with water and dried to afford (1-N-Fmoc-aminocyclopropyl)methanol, 1.90 g (100%). MS m/z 310 (M+H)+.

EXAMPLE 55

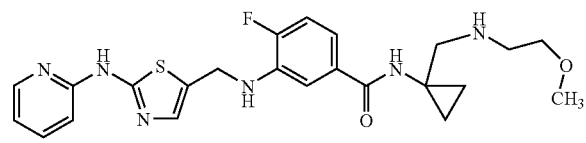

4-Fluoro-N-{1-[(2-methoxy-ethylamino)-methyl]-cyclopropyl}-3-{[2-(pyridin-2-ylamino)-thiazol-5-ylmethyl]-amino}-benzamide Step A To a solution of N-Fmoc aminocyclopropylcarboxylic acid (2.00 g, 6.19 mmol)in DCM (20 mL) and DMF (0.5 mL) was added a solution of oxalyl chloride (2 M in DCM, 10 mL) at RT. The mixture was stirred for 4 h. The mixture was concentrated and the residue was dissolved in THF (15 ml) and NaBH4 (470 mg, 12.4 mmol) was added. The mixture was refluxed for 2 h and poured onto ice. The solid was collected, washed with water and dried to afford (1-N-Fmoc-aminocyclopropyl)methanol, 1.90 g (100%). MS m/z 310 (M+H)+.

Step B

To a solution of N-Fmoc-aminocyclopropylcarboxylic acid (2.00 g, 6.19 mmol) in DCM (20 mL) and DMF (0.5 mL) was added a solution of oxalyl chloride (2 M in DCM, 10 mL) at RT. After stirring for 4 h the mixture was concentrated and the residue was dissolved in THF (15 ml) and NaBH$_4$ (470 mg, 12.4 mmol) was added. The resulting mixture was refluxed for 2 h and then poured onto ice. The solid formed was collected, washed with water and dried to afford (1-N-Fmoc-aminocyclopropyl)methanol (1.9 g, 100%). MS m/z 310 (M+H)$^+$.

Step C

To a solution of oxalyl chloride (2 M in DCM, 1.5 mL) at −20° C. was added DCM (5 mL), followed by DMSO (0.5 mL). After 10 min a solution of the compound 55B (309 mg, 1 mmol) in DCM (5 mL) was added. The mixture was allowed to warm up to RT, then cooled again to −20° C. and triethylamine (0.5 mL) was added. The resulting mixture was warmed up to RT and acidified with 1 N HCl solution. The organic layer was separated and washed with brine, dried and concentrated to afford (1-N-Fmoc-aminocyclopropyl)-carbaldehyde (compound 55C) as a solid, (145 mg, 47%). MS m/z 308 (M+H)$^+$.

Step D

A solution of the above aldehyde 55C (140 mg, 0.46 mmol) and methoxyethylamine (68 mg, 0.92 mmol) in acetic acid/DCM (1:1, 5 mL) was stirred at RT for 20 min, followed by addition of sodium triacetoxy borohydride (120 mg, 0.566 mmol). After 1 h, the solvent was removed and the residue was neutralized with NaHCO$_3$ solution. The mixture was extracted with ethyl acetate (3×10 mL) and the extract was dried and concentrated. The residue was dissolved in THF and Boc anhydride (100 mg, 0.47 mmol) was added. The mixture was stirred at RT for 1 h. The solvents were removed and residue was purified by column chromatograph (SiO2; EtOAC/hexanes 1:1 ) to afford (1-{[tert-butoxycarbonyl-(2-methoxy-ethyl)-amino]-methyl}-cyclopropyl)-carbamic acid 9H-fluoren-9-ylmethyl ester 130 mg (60%). MS m/z 467 (M+H)$^+$.

Step E

Compound 55D (130 mg, 0.28 mmol) was dissolved in DCM (2 mL) and stirred with pyrrolidine (0.1 mL) at RT for 2 h. The volatiles were removed, the residue was triturated with MeOH and the solid was filtered off. The filtrate solution was concentrated to afford (1-Amino-cyclopropyl-methyl)-(2-methoxyethyl)-carbamic acid tert-butyl ester as an oil (65 mg, 95%). MS m/z 245 (M+H)$^+$.

Step F

Compound 55E was coupled with compound 52A in manner similar to the preparation of Example 53 to afford [1-(4-fluoro-3-{[2-(pyridin-2-ylamino)-thiazol-5-ylmethyl]-amino}-benzoylamino)cyclopropylmethyl]-(2-methoxyethyl)carbamic acid tert-butyl ester. This compound was then treated with TFA in dichloromethane (1:1) at RT for 1 h. The reaction mixture was neutralized with NaHCO₃ solution and extracted DCM. The organic layer was concentrated to afford the title compound in 40% yield. MS m/z 471 (M+H)⁺.

EXAMPLE 56

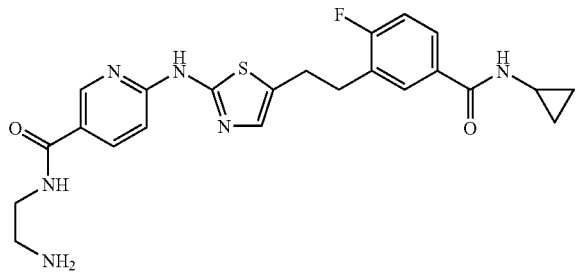

N-(3-Aminoethyl)-6-{5-[2-(5-cyclopropylcarbamoyl-2-fluoro-phenyl)-ethyl]-thiazol-2-ylamino}-nicotinamide Step A A mixture of ethyl-6-amino-nicotinate (2.5 g, 15 mmol) and benzoyl isothiocyanate (2.45 g, 15 mmol) in THF (20 mL) was heated at 40° C. for 4 h. To this mixture at RT, was added sodium ethoxide (2.04 g, 30 mmol) in ethanol (10 mL). After stirring the resulting mixture at RT for 16 h, the volatiles were removed in vacuo. The residue was suspended in aqueous NH₄Cl and the solid formed was collected by filtration, rinsed with water and dried to afford 6-thioureido-nicotinic acid ethyl ester as a white solid (2.6 g, 77% yield). LC/MS; (M+H)⁺=226.

Step B

The above compound was treated with compound 13A by a procedure similar to that described in procedure 13B to afford 6-{5-[2-(5-cyclopropylcarbamoyl-2-fluorophenyl)-ethyl]-thiazol-2-ylamino}-nicotinic acid ethyl ester. LC/MS; (M+H)⁺=443

Step C

Compound 56B in aq. NaOH (2M, 2 ml) and MeOH (3 ml) was heated at 50° C. for 5 h. The volatiles were removed in vacuo, and the residue was acidified with HCl(2N) to pH 6. The solid was collected by filtration, rinsed with H₂O, and dried in vacuo, to afford the acid intermediate (39%) as a brown solid. This acid was then converted to the title compound by a procedure similar to 19D. LC/MS; (M+H)⁺=469.

The following compounds were made from compound 56B by a procedure similar to the one described in 56C.

| Ex. # | Structure | Name | LC/MS; (M + H)⁺ |
|---|---|---|---|
| 57 | 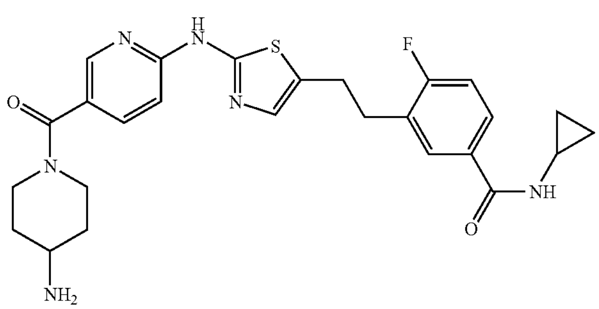 | 3-(2-{2-[5-(4-Amino-piperidine-1-carbonyl)-pyridin-2-ylamino]-thiazol-5-yl}-ethyl)-N-cyclopropyl-4-fluorobenzamide | 509 |
| 58 | 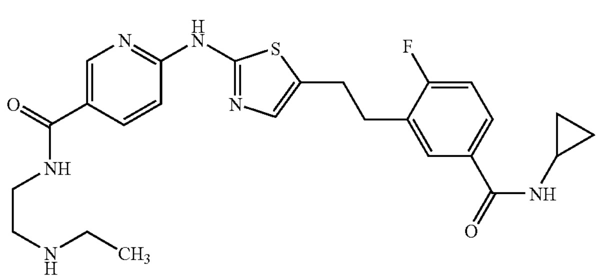 | 6-{5-[2-(5-Cyclopropylcarbamoyl-2-fluoro-phenyl)-ethyl]-thiazol-2-ylamino}-N-(2-ethylamino-ethyl)-nicotinamide | 497 |

| Ex. # | Structure | Name | LC/MS; (M + H)+ |
|---|---|---|---|
| 59 | 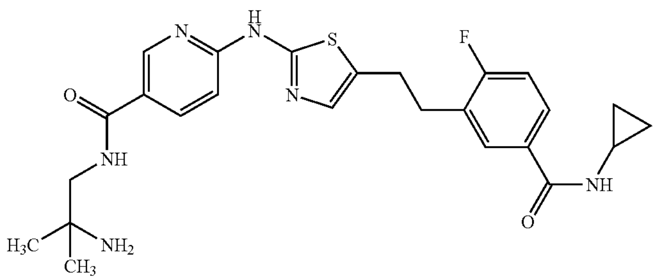 | N-(2-Amino-2-methyl-propyl)-6-{5-[2-(5-cyclopropylcarbamoyl-2-fluoro-phenyl)-ethyl]-thiazol-2-ylamino}-nicotinamide | 497 |
| 60 | 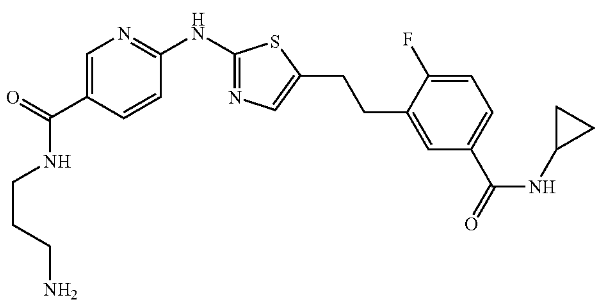 | N-(3-Aminopropyl)-6-{5-[2-(5-cyclopropylcarbamoyl-2-fluoro-phenyl)-ethyl]-thiazol-2-ylamino}-nicotinamide | 483 |

EXAMPLE 61

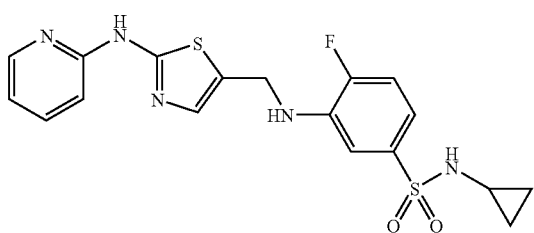

N-Cyclopropyl-4-fluoro-3-{[2-(pyridin-2-ylamino)-thiazol-5-ylmethyl]-amino}-benzenesulfonamide Step A To a solution of fuming nitric acid (8 mL) and conc. $H_2SO_4$ (16 mL), was added 4-fluorobenzenesulfonyl chloride (1.3 g, 6.7 mmol) in small portions. The mixture was stirred at RT for 2 h. and then poured onto crushed ice (60 g) and extracted with dichloromethane (2×). The organic layer was washed with brine, dried over $Na_2SO_4$, filtered and concentrated. The residue was dissolved in $CH_2Cl_2$ (30 mL) cooled to −40° C. and cyclopropylamine (388 mg, 6.8 mmol), followed by DIPEA (8 mmol) were added. After stirring at −40° C. for 2 h, the mixture was poured on 5% citric acid solution and extracted with dichloromethane. The organic layer was separated, and passed through a short pad of silica gel and concentrated in vacuo to afford N-cyclopropyl-4-fluoro-3-nitrobenzenesulfonamide (1.6 g, 92%) as a yellow solid.

Step B

The mixture of N-cyclopropyl-4-fluoro-3-nitrobenzenesulfonamide (520 mg, 2 mmol) and Pd/C (10%, 100 mg) in EtOH was hydrogenated (1 atm) overnight. The mixture was filtered through a short pad of celite and concentrated in vacuo to afford N-cyclopropyl-4-fluoro-3-aminobenzenesulfonamide (440 mg, 95%) as an ivory solid. LC/MS; (M+H)+=231.

Step C

Compound 61B was converted to the title compound in a manner similar to the preparation of Example 1. LC/MS; (M+H)+=420.

The following compounds were prepared from acid 52A by a procedure similar to the preparation of Example 53 or procedure 19D via t-BOC protected amine.

| Ex. # | Structure | Name | Yield % | LC/MS (M + H)+ |
|---|---|---|---|---|
| 62 | 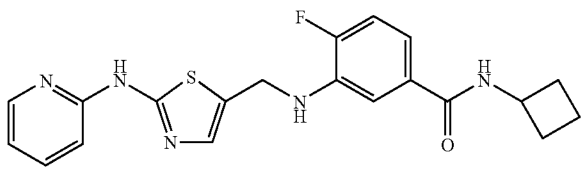 | N-Cyclobutyl-4-fluoro-3-{[2-(pyridin-2-ylamino)-thiazol-5-ylmethyl]-amino}-benzamide | 75 | 398 |
| 63 | 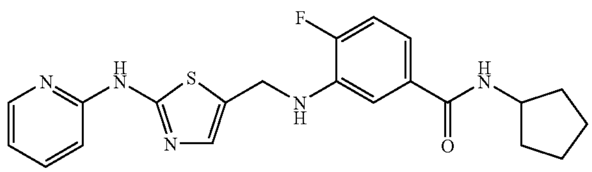 | N-Cyclopentyl-4-fluoro-3-{[2-(pyridin-2-ylamino)-thiazol-5-ylmethyl]-amino}-benzamide | 68 | 412 |
| 64 | 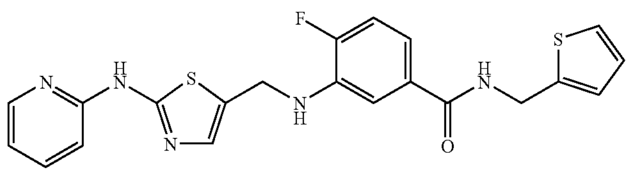 | 4-Fluoro-3-{[2-(pyridin-2-ylamino)-thiazol-5-ylmethyl]-amino}-N-thiophen-2-ylmethylbenzamide | 86 | 440 |
| 65 | 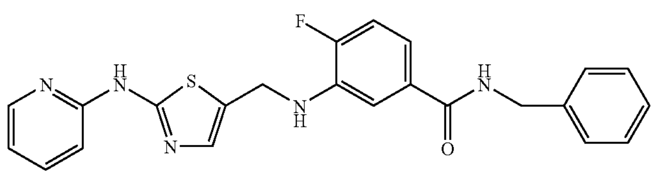 | N-Benzyl-4-fluoro-3-{[2-(pyridin-2-ylamino)-thiazol-5-ylmethyl]-amino}-benzamide | 85 | 452 |
| 66 | 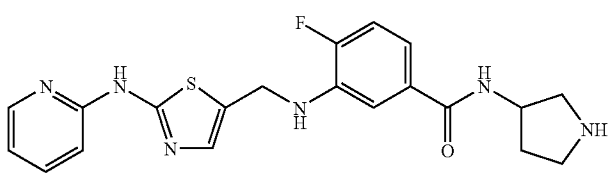 | R-4-Fluoro-3-{[2-(pyridin-2-ylamino)-thiazol-5-ylmethyl]-amino}-N-pyrrolidin-3-yl-benzamide | 79 | 431 |
| 67 | 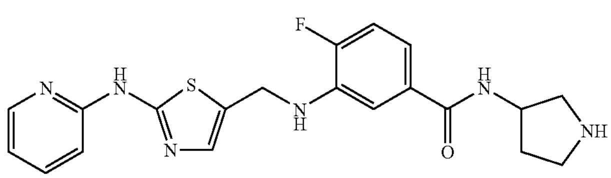 | S-4-Fluoro-3-{[2-(pyridin-2-ylamino)-thiazol-5-ylmethyl]-amino}-N-pyrrolidin-3-yl-benzamide | 65 | 431 |
| 68 | 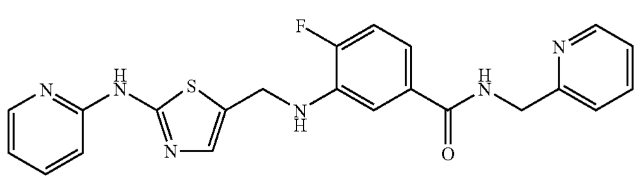 | 4-Fluoro-3-{[2-(pyridin-2-ylamino)-thiazol-5-ylmethyl]-amino}-N-pyridin-2-ylmethylbenzamide | 76 | 435 |
| 69 | 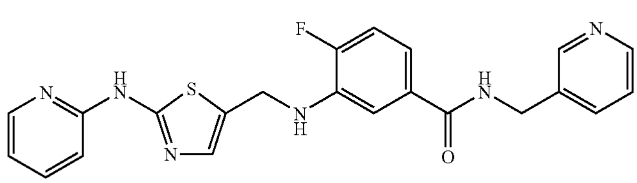 | 4-Fluoro-3-{[2-(pyridin-2-ylamino)-thiazol-5-ylmethyl]-amino}-N-pyridin-3-ylmethylbenzamide | 64 | 435 |

-continued

| Ex. # | Structure | Name | Yield % | LC/MS (M + H)+ |
|---|---|---|---|---|
| 70 | 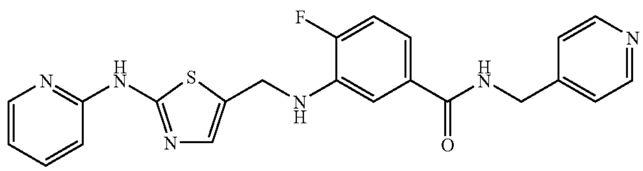 | 4-Fluoro-3-{[2-(pyridin-2-ylamino)-thiazol-5-ylmethyl]-amino}-N-pyridin-4-ylmethylbenzamide | 65 | 435 |
| 71 | 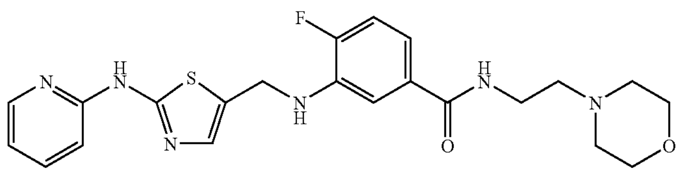 | 4-Fluoro-N-(2-morpholin-4-yl-ethyl)-3-{[2-(pyridin-2-ylamino)-thiazol-5-ylmethyl]-amino}-benzamide | 66 | 475 |
| 72 | 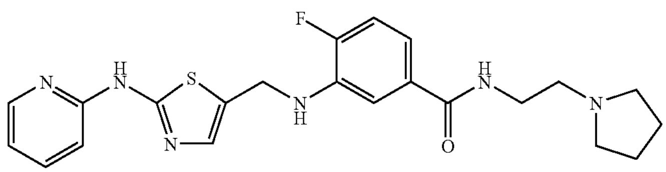 | 4-Fluoro-3-{[2-(pyridin-2-ylamino)-thiazol-5-ylmethyl]-amino}-N-(2-pyrrolidin-1-yl-ethyl)-benzamide | 60 | 441 |
| 73 | 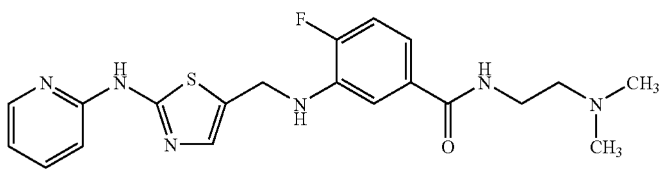 | N-(2-Dimethylamino-ethyl)-4-fluoro-3-{[2-(pyridin-2-ylamino)-thiazol-5-ylmethyl]-amino}-benzamide | 73 | 415 |
| 74 | 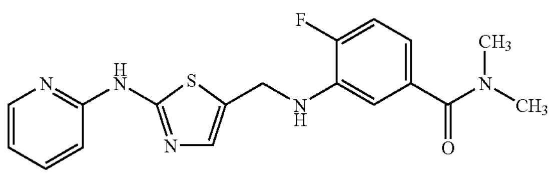 | 4-Fluoro-N,N-dimethyl-3-{[2-(pyridin-2-ylamino)-thiazol-5-ylmethyl]-amino}-benzamide | 80 | 372 |
| 75 | 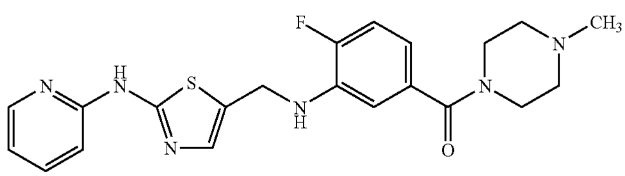 | (4-Fluoro-3-{[2-(pyridin-2-ylamino)-thiazol-5-ylmethyl]-amino}-phenyl)-(4-methyl-piperazin-1-yl)-methanone | 80 | 427 |
| 76 | 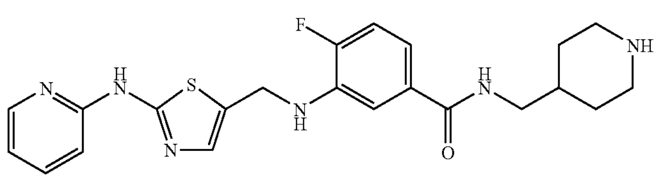 | 4-Fluoro-N-piperidin-4-ylmethyl-3-{[2-(pyridin-2-ylamino)-thiazol-5-ylmethyl]-amino}-benzamide | 50 | 441 |
| 77 | 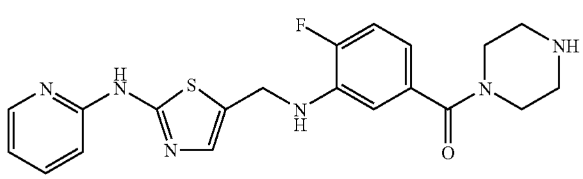 | (4-Fluoro-3-{[2-(pyridin-2-ylamino)-thiazol-5-ylmethyl]-amino}-phenyl)-piperazin-1-yl-methanone | 60 | 413 |

-continued

| Ex. # | Structure | Name | Yield % | LC/MS (M + H)+ |
|---|---|---|---|---|
| 78 | 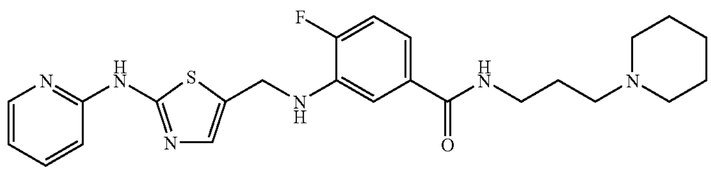 | 4-Fluoro-N-(3-piperidin-1-yl-propyl)-3-{[2-(pyridin-2-ylamino)-thiazol-5-ylmethyl]-amino}-benzamide | 76 | 469 |
| 79 | 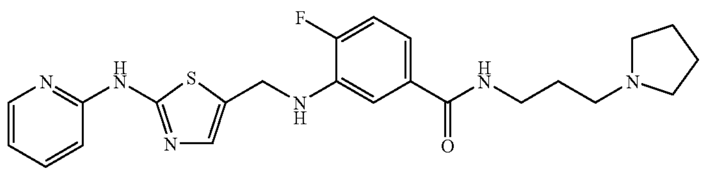 | 4-Fluoro-3-{[2-(pyridin-2-ylamino)-thiazol-5-ylmethyl]-amino}-N-(3-pyrrolidin-1-yl-propyl)-benzamide | 80 | 455 |
| 80 | 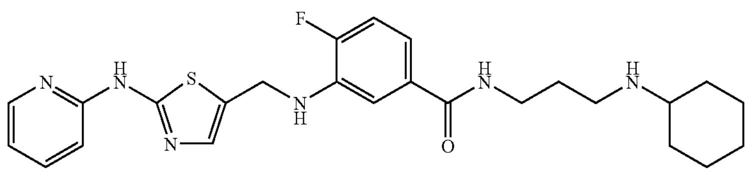 | N-(3-Cyclohexylamino-propyl)-4-fluoro-3-{[2-(pyridin-2-ylamino)-thiazol-5-ylmethyl]-amino}-benzamide | 65 | 483 |
| 81 | 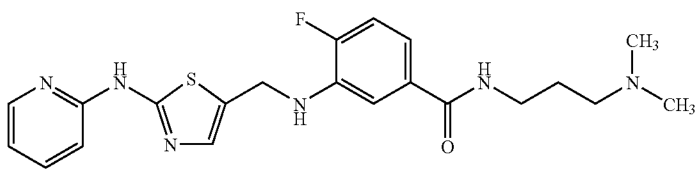 | N-(3-Dimethylamino-propyl)-4-fluoro-3-{[2-(pyridin-2-ylamino)-thiazol-5-ylmethyl]-amino}-benzamide | 85 | 429 |
| 82 | 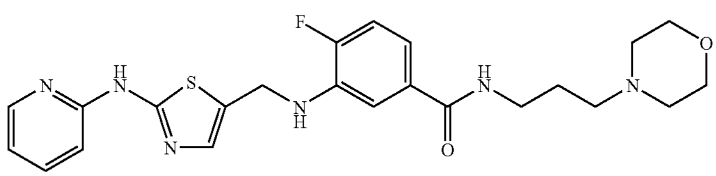 | 4-Fluoro-N-(3-morpholin-4-yl-propyl)-3-{[2-(pyridin-2-ylamino)-thiazol-5-ylmethyl]-amino}-benzamide | 70 | 471 |
| 83 | 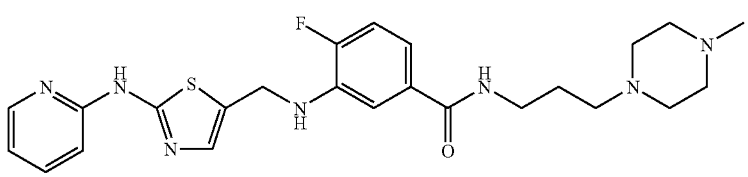 | 4-Fluoro-N-[3-(4-methyl-piperazin-1-yl)-propyl]-3-{[2-(pyridin-2-ylamino)-thiazol-5-ylmethyl]-amino}-benzamide | 86 | 485 |
| 84 | 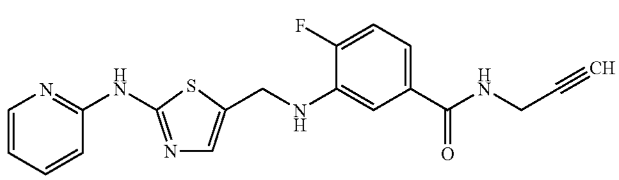 | 4-Fluoro-N-prop-2-ynyl-3-{[2-(pyridin-2-ylamino)-thiazol-5-ylmethyl]-amino}-benzamide | 88 | 381 |
| 85 | 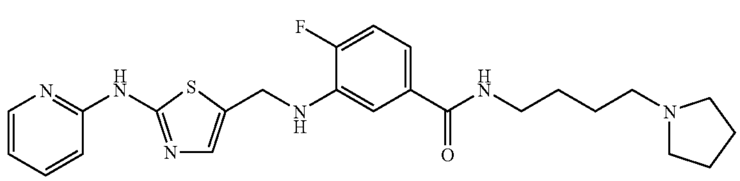 | 4-Fluoro-3-{[2-(pyridin-2-ylamino)-thiazol-5-ylmethyl]-amino}-N-(4-pyrrolidin-1-yl-butyl)-benzamide | 80 | 469 |

-continued

| Ex. # | Structure | Name | Yield % | LC/MS (M + H)+ |
|---|---|---|---|---|
| 86 | 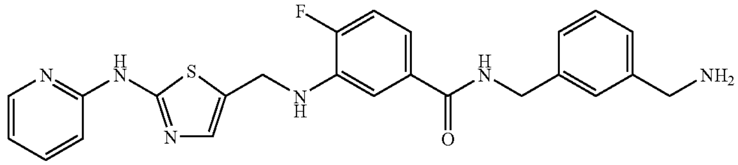 | N-(3-Aminomethyl-benzyl)-4-fluoro-3-{[2-(pyridin-2-ylamino)-thiazol-5-ylmethyl]-amino}-benzamide | 60 | 463 |
| 87 | 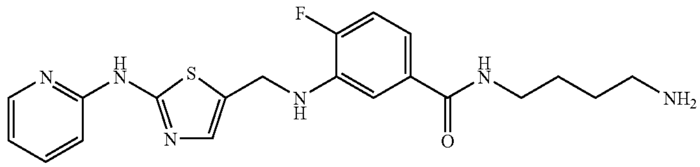 | N-(4-Amino-butyl)-4-fluoro-3-{[2-(pyridin-2-ylamino)-thiazol-5-ylmethyl]-amino}-benzamide | 70 | 401 |
| 88 | 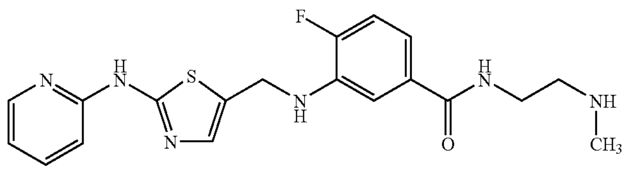 | 4-Fluoro-N-(2-methylamino-ethyl)-3-{[2-(pyridin-2-ylamino)-thiazol-5-ylmethyl]-amino}-benzamide | 70 | 401 |
| 89 | 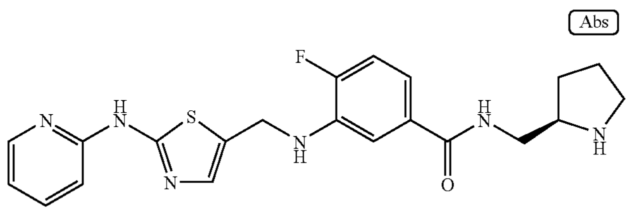 | 4-Fluoro-3-{[2-(pyridin-2-ylamino)-thiazol-5-ylmethyl]-amino}-N-pyrrolidin-2-ylmethyl-benzamide | 75 | 427 |
| 90 | 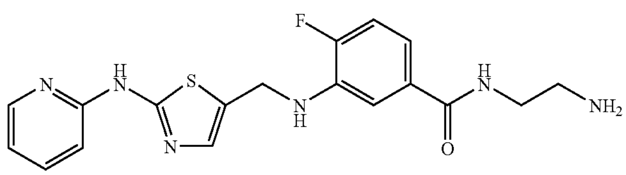 | N-(2-Amino-ethyl)-4-fluoro-3-{[2-(pyridin-2-ylamino)-thiazol-5-ylmethyl]-amino}-benzamide | 86 | 397 |
| 91 | 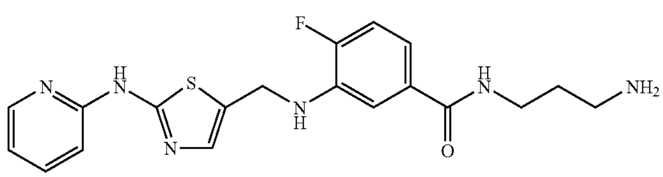 | N-(3-Amino-propyl)-4-fluoro-3-{[2-(pyridin-2-ylamino)-thiazol-5-ylmethyl]-amino}-benzamide | 80 | 421 |
| 92 | 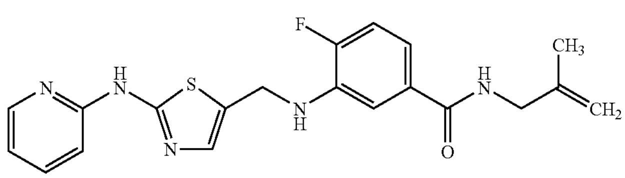 | 4-Fluoro-N-(2-methyl-allyl)-3-{[2-(pyridin-2-ylamino)-thiazol-5-ylmethyl]-amino}-benzamide | 77 | 398 |
| 93 | 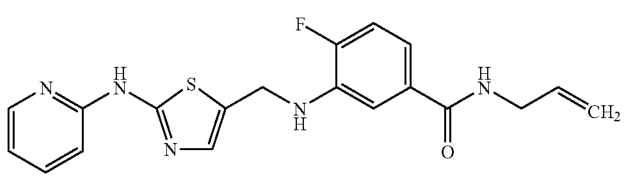 | N-Allyl-4-fluoro-3-{[2-(pyridin-2-ylamino)-thiazol-5-ylmethyl]-amino}-benzamide | 75 | 384 |

-continued

| Ex. # | Structure | Name | Yield % | LC/MS (M + H)+ |
|---|---|---|---|---|
| 94 | 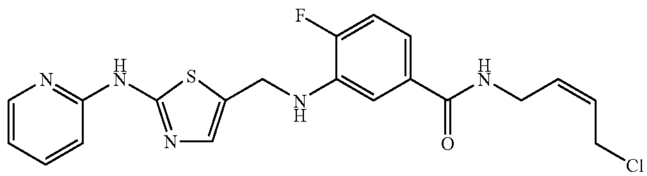 | N-(4-Chloro-but-2-enyl)-4-fluoro-3-{[2-(pyridin-2-ylamino)-thiazol-5-ylmethyl]-amino}-benzamide | 34 | 432 |
| 95 | 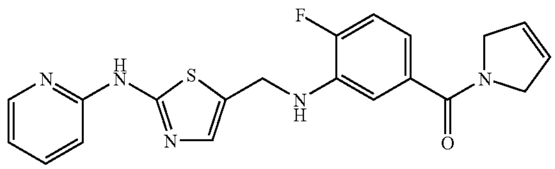 | (2,5-Dihydro-pyrrol-1-yl)-(4-fluoro-3-{[2-(pyridin-2-ylamino)-thiazol-5-ylmethyl]-amino}-phenyl)-methanone | 30 | 396 |
| 96 | 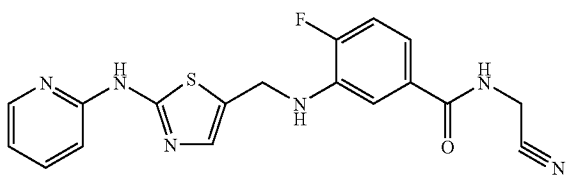 | N-Cyanomethyl-4-fluoro-3-{[2-(pyridin-2-ylamino)-thiazol-5-ylmethyl]-amino}-benzamide | 19 | 383 |
| 97 | 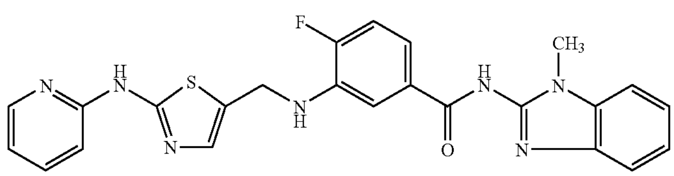 | 4-Fluoro-N-(1-methyl-1H-benzimidazol-2-yl)-3-{[2-(pyridin-2-ylamino)-thiazol-5-ylmethyl]-amino}-benzamide | 85 | 474 |
| 98 | 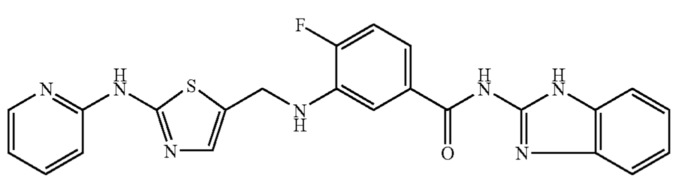 | N-(1H-Benzoimidazol-2-yl)-4-fluoro-3-{[2-(pyridin-2-ylamino)-thiazol-5-ylmethyl]-amino}-benzamide | 77 | 460 |
| 99 | 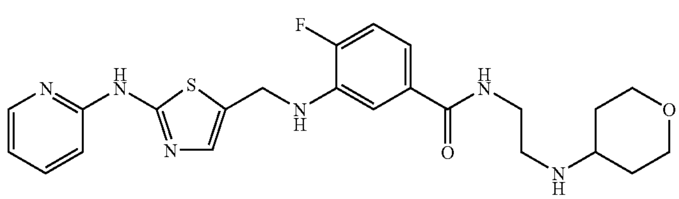 | 4-Fluoro-3-{[2-(pyridin-2-ylamino)-thiazol-5-ylmethyl]-amino}-N-[2-(tetrahydro-pyran-4-ylamino)-ethyl]-benzamide | 60 | 471 |

The following compounds were prepared in a manner similar to the reparation of Example 18 except 4-fluoro-3-nitrobenzoic acid was used.

EXAMPLE 100

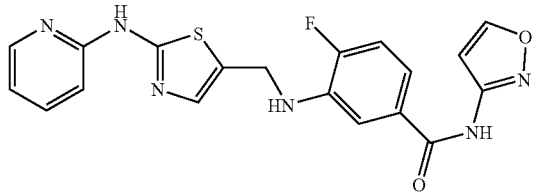

4-Fluoro-N-isoxazol-3-yl-3-{[2-(pyridin-2-ylamino)-thiazol-5-ylmethyl]-amino}-benzamide
LC/MS; (M+H)+=411

EXAMPLE 101

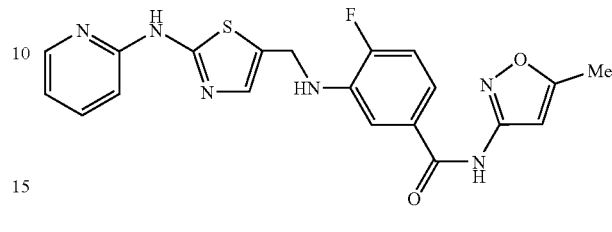

4-Fluoro-N-(5-methyl-isoxazol-3-yl)-3-{[2-(pyridin-2-ylamino)-thiazol-5-ylmethyl]-amino}-benzamide

LC/MS; (M+H)+=425

The following compounds were prepared in a manner similar to the preparation of Example 52 except 2,4-difluoro5-aminobenzoic acid was used.

| Ex. # | Structure | Name | Yield % | LC/MS (M + H)+ |
|---|---|---|---|---|
| 102 | 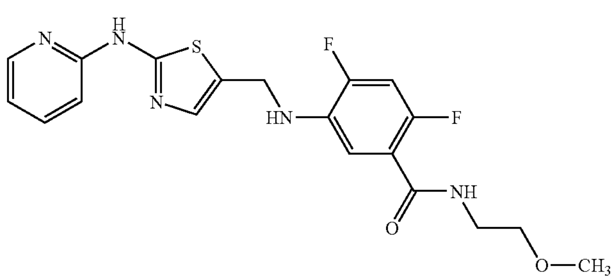 | 2,4-Difluoro-N-(2-methoxy-ethyl)-5-{[2-(pyridin-2-ylamino)-thiazol-5-ylmethyl]-amino}-benzamide | 60 | 420 |
| 103 | 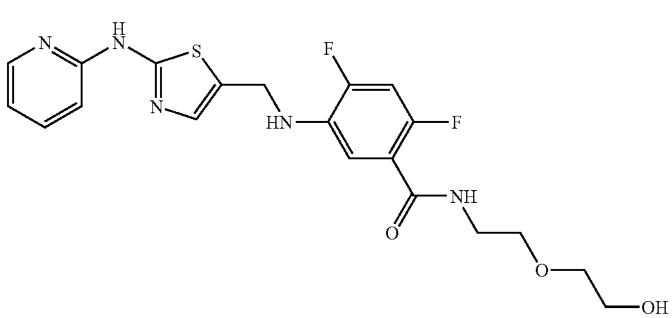 | 2,4-Difluoro-N-[2-(2-hydroxy-ethoxy)-ethyl]-5-{[2-(pyridin-2-ylamino)-thiazol-5-ylmethyl]-amino}-benzamide | 69 | 450 |

-continued

| Ex. # | Structure | Name | Yield % | LC/MS (M + H)+ |
|---|---|---|---|---|
| 104 | 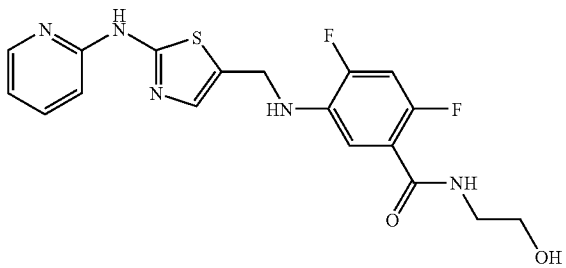 | 2,4-Difluoro-N-(2-hydroxy-ethyl)-5-{[2-(pyridin-2-ylamino)-thiazol-5-ylmethyl]-amino]-benzamide | 59 | 406 |
| 105 | 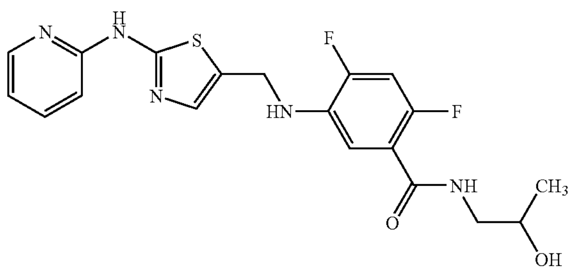 | R-2,4-Difluoro-N-(2-hydroxy-propyl)-5-{[2-(pyridin-2-ylamino)-thiazol-5-ylmethyl]-amino}-benzamide | 55 | 420 |
| 106 | 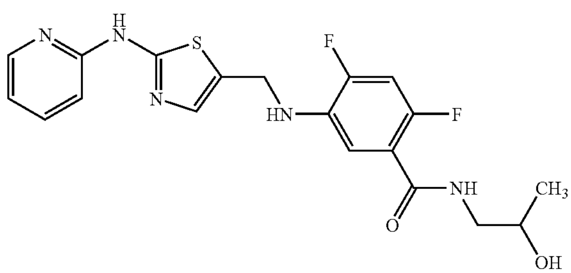 | S-2,4-Difluoro-N-(2-hydroxy-propyl)-5-{[2-(pyridin-2-ylamino)-thiazol-5-ylmethyl]-amino}-benzamide | 59 | 420 |

EXAMPLE 107

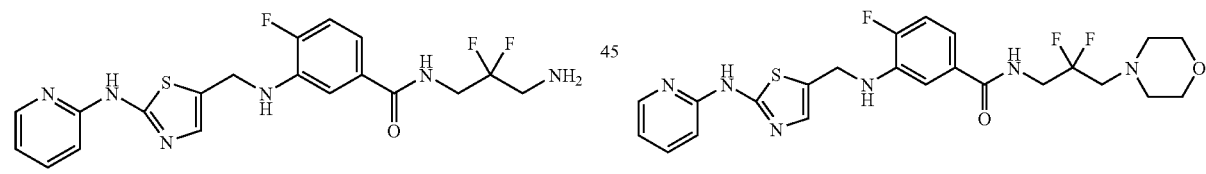

N-(3-Amino-2,2-difluoro-propyl)-4-fluoro-3-{[2-(pyridin-2-ylamino)-thiazol-5-ylmethyl]-amino}-benzamide To a mixture of 4-fluoro-3-{[2-(pyridin-2-ylamino)-thiazol-5-ylmethyl]-amino}-benzoic acid (compound 52A, 21 mg, 0.06 mmol) and HATU (38 mg, 0.1 mmol) in DMF (0.2 ml) and THF (0.4 ml), were added 2,2-difluoro-1,3-propanediamine (ref. *Tetrahedron,* 8617, 1994) (60 mg, 0.54 mmol) and DIPEA (26 mg, 0.2 mmol). The resulting mixture was stirred at RT for 18 h, then diluted with CH$_2$Cl$_2$, washed with brine, dried over Na$_2$SO$_4$ and concentrated. The residue was purified by flash column chromatography [silica gel, 5% (NH$_3$/MeOH(2M) in EtOAc] to afford the title compound (17 mg, 65%) as a white solid. LC/MS; (M+H)+=437.

EXAMPLE 108

N-(2,2-Difluoro-3-morpholin-4-yl-propyl)-4-fluoro-3-{[2-(pyridin-2-ylamino)-thiazol-5-ylmethyl]-amino}-benzamide A solution of dihydrofuran (35 mg, 0.5 mmol) in MeOH (1.5 mL) was treated with ozone at −78° C. until the solution turned blue. Argon was streamed through the solution to remove excess ozone. The solution was warmed to 0° C., and N-(3-Amino-2,2-difluoro-propyl)-4-fluoro-3-{[2-(pyridin-2-ylamino)-thiazol-5-ylmethyl]-amino}-benzamide (Example 107) (12 mg, 0.027 mmol)) followed by NaBH(OAc)$_3$ (84 mg) were added over a period of 3 h. The mixture was diluted with CH$_2$Cl$_2$, washed with sat. NaHCO$_3$, dried over Na$_2$SO$_4$ and concentrated. The residue was purified by flash column chromatography [silica gel, 1% (NH$_3$/MeOH(2M) in EtOAc] to afford the title compound (7 mg, 51%) as a white solid. LC/MS; (M+H)⁺=507. ¹HNMR (CD₃OD): δ 2.47 (m, 4H); 2.66 (t, 2H, J=13.7 Hz); 3.53 (m, 4H); 3.80 (t, 2H, J=14.3 Hz); 4.48 (s, 2H); 6.78 (m, 1H); 6.86 (d, 1H, J=8.25 Hz); 7.0 (m, 2H); 7.15 (s, 1H); 7.23 (m, 1H); 7.54 (m, 1H), 8.15 (d, 1H, J=4.4 Hz).

EXAMPLE 109

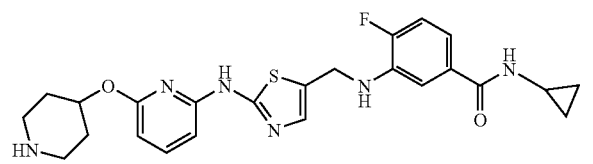

N-Cyclopropyl-4-fluoro-3-({2-[6-(piperidin-4-yloxy)-pyridin-2-ylamino]-thiazol-5-ylmethyl}-amino)-benzamide Step A 2-Bromo-6-amino-pyridine was converted to 3-{[2-(6-Bromo-pyridin-2-ylamino)-thiazol-5-ylmethyl]-amino}-N-cyclopropyl-4-fluoro-benzamide by a procedure similar to the preparation of Example 19.

Step B

To a solution of 4-hydroxy-piperidine-1-carboxylic acid tert-butyl ester (100 mg, 0.5 mmol) in dioxane (2 mL) at RT, was added NaH (60% in mineral oil, 0.6 mmol). After stirring the mixture at RT for 15 min, compound 109A (25 mg, 0.054 mmol) and Cu powder (15 mg) were added. The resulting mixture was heated at 170° C. in a sealed tube for 20 min. After cooling to RT, the mixture was diluted with EtOAc and filtered through a short pad of celite. The filtrate was concentrated, and purified by flash column chromatography (silica gel, 20% EtOAc/CH₂Cl₂ to 100% EtOAc) to afford the coupled intermediate (15 mg, 58% yield) as a beige solid, which was treated with 30% TFA/CH₂Cl₂ (3 mL) for 30 min. The volatiles were removed, and the residue was purified by preparative HPLC to afford the title compound (7 mg, 47% yield) as a white solid. LC/MS; (M+H)⁺= 483.

EXAMPLE 110

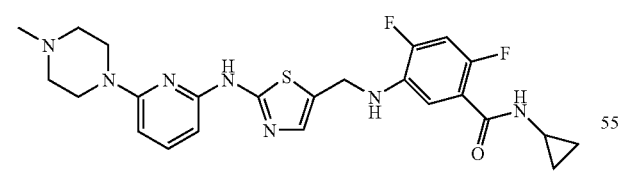

N-Cyclopropyl-2,4-difluoro-5-({2-[6-(4-methyl-piperazin-1-yl)-pyridin-2-ylamino]-thiazol-5-ylmethyl}-amino)-benzamide A mixture of 5-{[2-(6-bromo-pyridin-2-ylamino)-thiazol-5-ylmethyl]-amino}-N-cyclopropyl-2,4-difluoro-benzamide (96 mg, 0.20 mmol) in neat N-methyl piperazine (0.4 mL) was heated to 120° C. in a sealed tube for 5 h. The reaction mixture was cooled to RT, diluted with methylene chloride (5 mL), and washed with water (2×5 mL). The organic layer was dried over Na₂SO₄, concentrated, and the residue was purified by silica gel eluted with 2-10% MeOH/CH₃Cl to give the title compound (53 mg, 55%) as a light yellow solid. (M+H)⁺=500.

What is claimed is:

1. A compound of formula I

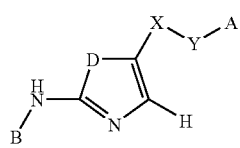

wherein
  A is substituted aryl;
  B is heteroaryl or substituted heteroaryl;
  X is independently selected from the group consisting of $R^1CR^2$, S, O, $SO_2$, SO and $NR^3$, with the proviso that at least one of X and Y is $R^1CR^2$;
  Y is O;
  D is S;
  $R^1$, $R^2$, $R^3$ are independently selected from the group consisting of hydrogen, alkyl, substituted alkyl, aryl, substituted aryl, heterocyclo, substituted heterocyclo, aralkyl, arylalkyl, substituted aralkyl, $COR^5$ and $SO_2R^6$;
  $R^5$ and $R^6$ are independently selected from the group consisting of alkyl, substituted alkyl, aryl, substituted aryl, heterocyclo, substituted heterocyclo, heteroaryl, substituted heteroaryl, aralkyl, substituted aralkyl, heterocycloalkyl and substituted heterocycloalkyl; and
  its enantiomers, diastereomers, and pharmaceutically acceptable salts, prodrugs and solvates thereof.

2. A compound of the formula

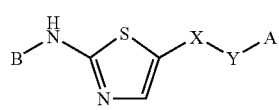

wherein
  B is a pyridinyl group optionally substituted with 1–4 substituents;
  A is substituted aryl,
  X is independently selected from the group consisting of $R^1CR^2$, S, O, $SO_2$, SO and $NR^3$, with the proviso that at least one of X and Y is $R^1CR^2$;
  Y is O;
  and its enantiomers, diastereomers, and pharmaceutically acceptable salts, prodrugs and solvates thereof.

3. A compound of claim 2 wherein A is a substituted benzamide.

4. A pharmaceutical composition comprising a compound of claim 1 and a pharmaceutically acceptable carrier.

* * * * *